(12) United States Patent
Gregory et al.

(10) Patent No.: US 11,712,508 B2
(45) Date of Patent: Aug. 1, 2023

(54) SYSTEMS AND METHODS FOR DIRECTLY INTERACTING WITH COMMUNICATIONS MODULE OF WOUND THERAPY APPARATUS

(71) Applicant: Smith & Nephew, Inc., Memphis, TN (US)

(72) Inventors: William W. Gregory, Gainesville, FL (US); Edward Yerbury Hartwell, Hull (GB); Felix Clarence Quintanar, Hull (GB)

(73) Assignee: Smith & Nephew, Inc., Memphis, TN (US)

(*) Notice: Subject to any disclaimer, the term of this patent is extended or adjusted under 35 U.S.C. 154(b) by 744 days.

(21) Appl. No.: 16/629,190

(22) PCT Filed: Jul. 9, 2018

(86) PCT No.: PCT/US2018/041313
§ 371 (c)(1),
(2) Date: Jan. 7, 2020

(87) PCT Pub. No.: WO2019/014141
PCT Pub. Date: Jan. 17, 2019

(65) Prior Publication Data
US 2020/0222599 A1 Jul. 16, 2020

Related U.S. Application Data

(60) Provisional application No. 62/530,480, filed on Jul. 10, 2017.

(51) Int. Cl.
*G08B 23/00* (2006.01)
*A61M 1/00* (2006.01)
(Continued)

(52) U.S. Cl.
CPC ............. *A61M 1/96* (2021.05); *A61M 1/98* (2021.05); *G16H 20/40* (2018.01); *G16H 40/67* (2018.01);
(Continued)

(58) Field of Classification Search
CPC ............. A61M 1/90; A61M 2205/15; A61M 2205/18; A61M 2205/3569;
(Continued)

(56) References Cited

U.S. PATENT DOCUMENTS

| 695,270 A | 3/1902 | Beringer |
| 3,194,239 A | 7/1965 | Sullivan et al. |

(Continued)

FOREIGN PATENT DOCUMENTS

| CN | 102961815 A | 3/2013 |
| CN | 104721892 A | 6/2015 |

(Continued)

OTHER PUBLICATIONS

International Search Report and Written Opinion, re PCT Application No. PCT/US2018/041313, dated Sep. 25, 2018.
(Continued)

*Primary Examiner* — Anh V La
(74) *Attorney, Agent, or Firm* — Knobbe, Martens, Olson & Bear, LLP

(57) ABSTRACT

Embodiments of negative pressure wound therapy systems and methods are disclosed. In some embodiments, a wound therapy system includes a negative pressure source configured to provide negative pressure via a fluid flow path to a wound dressing, a first circuit board assembly including a first controller configured to control a wound therapy with the wound dressing by activation and deactivation of the negative pressure source, and a second circuit board assembly in communication with the first circuit board assembly,
(Continued)

the second circuit board assembly separate from the first circuit board assembly. The second circuit board assembly can include a second controller configured to wirelessly communicate therapy data via a communication network, receive an executable command from an electronic device, and execute the executable command without providing the executable command to the first controller.

22 Claims, 22 Drawing Sheets

(51) Int. Cl.
  *G16H 20/40* (2018.01)
  *G16H 40/67* (2018.01)
  *G06F 9/445* (2018.01)

(52) U.S. Cl.
  CPC ......... *A61M 1/982* (2021.05); *A61M 2205/15* (2013.01); *A61M 2205/18* (2013.01); *A61M 2205/3569* (2013.01); *A61M 2205/505* (2013.01); *A61M 2205/52* (2013.01); *A61M 2205/583* (2013.01); *A61M 2205/584* (2013.01); *A61M 2205/70* (2013.01); *G06F 9/44505* (2013.01)

(58) Field of Classification Search
  CPC ........ A61M 2205/505; A61M 2205/52; A61M 2205/583; A61M 2205/584; A61M 2205/70; G16H 20/40; G16H 40/67; G06F 9/44505
  USPC ............... 604/319; 340/573.1, 603, 604, 611
  See application file for complete search history.

(56) References Cited

U.S. PATENT DOCUMENTS

| | | | |
|---|---|---|---|
| 4,832,299 A | 5/1989 | Gorton et al. |
| 5,219,428 A | 6/1993 | Stern |
| 5,473,536 A | 12/1995 | Wimmer |
| 5,960,403 A | 9/1999 | Brown |
| 6,055,506 A | 4/2000 | Frasca et al. |
| 6,336,900 B1 | 1/2002 | Alleckson et al. |
| 6,353,445 B1 | 3/2002 | Babula et al. |
| 6,375,614 B1 | 4/2002 | Braun et al. |
| 6,385,622 B2 | 5/2002 | Bouve et al. |
| 6,406,426 B1 | 6/2002 | Reuss et al. |
| 6,434,572 B2 | 8/2002 | Derzay et al. |
| 6,460,041 B2 | 10/2002 | Lloyd |
| 6,574,518 B1 | 6/2003 | Lounsberry et al. |
| 6,640,145 B2 | 10/2003 | Hoffberg et al. |
| 6,640,246 B1 | 10/2003 | Gary et al. |
| 6,675,131 B2 | 1/2004 | Hahn |
| 6,681,003 B2 | 1/2004 | Linder et al. |
| 6,723,046 B2 | 4/2004 | Lichtenstein et al. |
| 6,730,024 B2 | 5/2004 | Freyre et al. |
| 6,747,556 B2 | 6/2004 | Medema et al. |
| 6,779,024 B2 | 8/2004 | Delahuerga |
| 6,782,285 B2 | 8/2004 | Birkenbach et al. |
| 6,856,825 B2 | 2/2005 | Hahn |
| 6,868,528 B2 | 3/2005 | Roberts |
| 6,871,211 B2 | 3/2005 | Labounty et al. |
| 6,909,974 B2 | 6/2005 | Yung et al. |
| 6,912,481 B2 | 6/2005 | Breunissen et al. |
| 6,961,731 B2 | 11/2005 | Holbrook |
| 7,004,915 B2 | 2/2006 | Boynton et al. |
| 7,022,113 B2 | 4/2006 | Lockwood et al. |
| 7,051,012 B2 | 5/2006 | Cole et al. |
| 7,062,251 B2 | 6/2006 | Birkett et al. |
| 7,066,883 B2 | 6/2006 | Schmidt et al. |
| 7,103,578 B2 | 9/2006 | Beck et al. |
| 7,108,683 B2 | 9/2006 | Zamierowski |
| 7,120,488 B2 | 10/2006 | Nova et al. |
| 7,133,869 B2 | 11/2006 | Bryan et al. |
| 7,167,858 B2 | 1/2007 | Naeymi-Rad et al. |
| 7,212,829 B1 | 5/2007 | Lau et al. |
| 7,264,591 B2 | 9/2007 | Brown |
| 7,300,418 B2 | 11/2007 | Zaleski |
| 7,304,573 B2 | 12/2007 | Postma |
| 7,311,665 B2 | 12/2007 | Hawthorne et al. |
| 7,333,002 B2 | 2/2008 | Bixler et al. |
| 7,353,179 B2 | 4/2008 | Ott et al. |
| 7,384,267 B1 | 6/2008 | Franks et al. |
| 7,430,598 B2 | 9/2008 | Raden et al. |
| 7,430,608 B2 | 9/2008 | Noonan et al. |
| 7,438,705 B2 | 10/2008 | Karpowicz et al. |
| 7,451,002 B2 | 11/2008 | Choubey |
| 7,457,804 B2 | 11/2008 | Uber et al. |
| 7,460,872 B2 | 12/2008 | Millard et al. |
| 7,534,240 B1 | 5/2009 | Johnson |
| 7,598,855 B2 | 10/2009 | Scalisi et al. |
| 7,608,066 B2 | 10/2009 | Vogel |
| 7,627,334 B2 | 12/2009 | Cohen et al. |
| 7,649,449 B2 | 1/2010 | Fenske et al. |
| 7,671,733 B2 | 3/2010 | McNeal et al. |
| 7,684,999 B2 | 3/2010 | Brown |
| 7,698,156 B2 | 4/2010 | Martucci et al. |
| 7,734,764 B2 | 6/2010 | Weiner et al. |
| 7,749,164 B2 | 7/2010 | Davis |
| 7,758,555 B2 | 7/2010 | Kelch et al. |
| 7,779,153 B2 | 8/2010 | Van Den Heuvel et al. |
| 7,789,828 B2 | 9/2010 | Clapp |
| 7,794,438 B2 | 9/2010 | Henley et al. |
| 7,827,148 B2 | 11/2010 | Mori et al. |
| 7,865,375 B2 | 1/2011 | Lancaster et al. |
| 7,889,069 B2 | 2/2011 | Fifolt et al. |
| 7,890,887 B1 | 2/2011 | Linardos et al. |
| 7,912,823 B2 | 3/2011 | Ferrari et al. |
| 7,925,603 B1 | 4/2011 | Laidig et al. |
| 7,933,817 B2 | 4/2011 | Radl et al. |
| 7,976,519 B2 | 7/2011 | Bubb et al. |
| 7,981,098 B2 | 7/2011 | Boehringer et al. |
| 7,988,850 B2 | 8/2011 | Roncadi et al. |
| 8,015,443 B2 | 9/2011 | Adachi |
| 8,015,972 B2 | 9/2011 | Pirzada |
| 8,019,618 B2 | 9/2011 | Brown |
| 8,036,925 B2 | 10/2011 | Choubey |
| 8,054,950 B1 | 11/2011 | Hung et al. |
| 8,069,057 B2 | 11/2011 | Choubey et al. |
| 8,094,009 B2 | 1/2012 | Allen et al. |
| 8,126,735 B2 | 2/2012 | Dicks et al. |
| 8,130,095 B2 | 3/2012 | Allen et al. |
| 8,131,472 B2 | 3/2012 | Chow et al. |
| 8,180,750 B2 | 5/2012 | Wilmering et al. |
| 8,190,445 B2 | 5/2012 | Kuth et al. |
| 8,190,448 B2 | 5/2012 | Bajars et al. |
| 8,228,188 B2 | 7/2012 | Key et al. |
| 8,246,606 B2 | 8/2012 | Stevenson et al. |
| 8,249,894 B2 | 8/2012 | Brown |
| 8,255,241 B2 | 8/2012 | Cafer |
| 8,260,630 B2 | 9/2012 | Brown |
| 8,280,682 B2 | 10/2012 | Vock et al. |
| 8,284,046 B2 | 10/2012 | Allen et al. |
| 8,290,792 B2 | 10/2012 | Sekura |
| 8,291,337 B2 | 10/2012 | Gannin et al. |
| 8,323,263 B2 | 12/2012 | Wood et al. |
| 8,332,233 B2 | 12/2012 | Ott et al. |
| 8,332,236 B2 | 12/2012 | Yurko et al. |
| 8,334,768 B2 | 12/2012 | Eaton et al. |
| 8,337,482 B2 | 12/2012 | Wood et al. |
| 8,360,975 B1 | 1/2013 | Schwieterman et al. |
| 8,400,295 B1 | 3/2013 | Khaira |
| 8,422,377 B2 | 4/2013 | Weiner et al. |
| 8,424,517 B2 | 4/2013 | Sutherland et al. |
| 8,436,871 B2 | 5/2013 | Alberte |
| 8,439,882 B2 | 5/2013 | Kelch |
| 8,457,740 B2 | 6/2013 | Osche |
| 8,480,641 B2 | 7/2013 | Jacobs |
| 8,515,776 B2 | 8/2013 | Schoenberg |
| 8,532,764 B2 | 9/2013 | Duke |
| 8,540,688 B2 | 9/2013 | Eckstein et al. |
| 8,545,483 B2 | 10/2013 | Schwabe et al. |

(56) References Cited

U.S. PATENT DOCUMENTS

| | | |
|---|---|---|
| 8,554,195 B2 | 10/2013 | Rao |
| 8,554,902 B2 | 10/2013 | Ebert et al. |
| 8,558,964 B2 | 10/2013 | Bedingfield |
| 8,560,082 B2 | 10/2013 | Wei |
| 8,577,694 B2 | 11/2013 | Kanaan |
| 8,595,553 B2 | 11/2013 | Goertler et al. |
| 8,600,777 B2 | 12/2013 | Schoenberg et al. |
| 8,626,342 B2 | 1/2014 | Williams et al. |
| 8,626,526 B2 | 1/2014 | Lemke et al. |
| 8,630,660 B2 | 1/2014 | Ray et al. |
| 8,632,485 B2 | 1/2014 | Schlaeper et al. |
| 8,641,693 B2 | 2/2014 | Locke et al. |
| 8,659,420 B2 | 2/2014 | Salvat et al. |
| 8,676,597 B2 | 3/2014 | Buehler et al. |
| 8,689,008 B2 | 4/2014 | Rangadass et al. |
| 8,694,600 B2 | 4/2014 | Gaines et al. |
| 8,706,537 B1 | 4/2014 | Young et al. |
| 8,725,528 B2 | 5/2014 | Locke et al. |
| 8,756,078 B2 | 6/2014 | Collins et al. |
| 8,757,485 B2 | 6/2014 | Drees et al. |
| 8,758,315 B2 | 6/2014 | Chen et al. |
| 8,768,441 B2 | 7/2014 | De Zwart et al. |
| 8,769,625 B2 | 7/2014 | Wang et al. |
| 8,781,847 B2 | 7/2014 | Simms et al. |
| 8,795,171 B2 | 8/2014 | Adamczyk |
| 8,795,244 B2 | 8/2014 | Randolph et al. |
| 8,838,136 B2 | 9/2014 | Carnes et al. |
| 8,862,393 B2 | 10/2014 | Zhou et al. |
| 8,868,794 B2 | 10/2014 | Masoud et al. |
| 8,874,035 B2 | 10/2014 | Sherman et al. |
| 8,887,100 B1 | 11/2014 | Cook et al. |
| 8,890,656 B2 | 11/2014 | Pendse |
| 8,897,198 B2 | 11/2014 | Gaines et al. |
| 8,902,278 B2 | 12/2014 | Pinter et al. |
| 8,905,959 B2 | 12/2014 | Basaglia |
| 8,909,595 B2 | 12/2014 | Gandy et al. |
| 8,912,897 B2 | 12/2014 | Carnes |
| 8,922,377 B2 | 12/2014 | Carnes |
| 8,945,073 B2 | 2/2015 | Croizat et al. |
| 8,947,237 B2 | 2/2015 | Margon et al. |
| 8,978,026 B2 | 3/2015 | Charlton et al. |
| 8,996,393 B2 | 3/2015 | Sobie |
| 9,047,648 B1 | 6/2015 | Lekutai et al. |
| 9,058,634 B2 | 6/2015 | Buan et al. |
| 9,081,885 B2 | 7/2015 | Bangera et al. |
| 9,087,141 B2 | 7/2015 | Huang et al. |
| 9,092,705 B2 | 7/2015 | Zhuang |
| 9,098,114 B2 | 8/2015 | Potter et al. |
| 9,105,006 B2 | 8/2015 | Williamson |
| 9,114,054 B2 | 8/2015 | Bennett |
| 9,117,012 B2 | 8/2015 | Basaglia |
| 9,135,398 B2 | 9/2015 | Kaib et al. |
| 9,141,270 B1 | 9/2015 | Stuart et al. |
| 9,159,148 B2 | 10/2015 | Boyer et al. |
| 9,215,516 B2 | 12/2015 | Carnes et al. |
| 9,215,581 B2 | 12/2015 | Julian et al. |
| 9,230,420 B2 | 1/2016 | Lee et al. |
| 9,268,827 B2 | 2/2016 | Fernandez |
| 9,286,443 B2 | 3/2016 | Ford et al. |
| 9,323,893 B2 | 4/2016 | Berry et al. |
| 9,332,363 B2 | 5/2016 | Jain et al. |
| 9,338,819 B2 | 5/2016 | Meng et al. |
| 9,424,020 B2 | 8/2016 | Borges et al. |
| 9,427,159 B2 | 8/2016 | Chang |
| 9,436,645 B2 | 9/2016 | Al-Ali et al. |
| 9,436,800 B2 | 9/2016 | Forrester |
| 9,439,584 B1 | 9/2016 | De Vries et al. |
| 9,460,431 B2 | 10/2016 | Curry |
| 9,474,679 B2 | 10/2016 | Locke et al. |
| 9,483,614 B2 | 11/2016 | Ash et al. |
| 9,539,373 B2 | 1/2017 | Jones et al. |
| 9,545,466 B2 | 1/2017 | Locke et al. |
| 9,558,331 B2 | 1/2017 | Orona et al. |
| 9,585,565 B2 | 3/2017 | Carnes |
| 9,589,247 B2 | 3/2017 | Bolene et al. |
| 9,602,952 B2 | 3/2017 | Kang et al. |
| 9,629,986 B2 | 4/2017 | Patel et al. |
| 9,658,066 B2 | 5/2017 | Yuen et al. |
| 9,662,438 B2 | 5/2017 | Kamen et al. |
| 9,687,618 B2 | 6/2017 | Steinhauer et al. |
| 9,693,691 B2 | 7/2017 | Johnson |
| 9,700,462 B2 | 7/2017 | Debusk et al. |
| 9,716,757 B2 | 7/2017 | Fernandes |
| 9,740,825 B2 | 8/2017 | Sansale et al. |
| 9,741,084 B2 | 8/2017 | Holmes et al. |
| 9,787,842 B1 | 10/2017 | Brooksby et al. |
| 9,792,660 B2 | 10/2017 | Cannon et al. |
| 9,817,948 B2 | 11/2017 | Swank |
| 9,818,164 B2 | 11/2017 | Nolte et al. |
| 9,838,645 B2 | 12/2017 | Hyde et al. |
| 9,864,066 B2 | 1/2018 | Park et al. |
| 9,878,081 B2 | 1/2018 | Leiendecker et al. |
| 9,905,123 B2 | 2/2018 | Lawhorn |
| 9,928,478 B2 | 3/2018 | Ragusky et al. |
| 9,974,492 B1 | 5/2018 | Dicks et al. |
| 9,990,466 B2 | 6/2018 | Debusk et al. |
| 9,996,681 B2 | 6/2018 | Suarez et al. |
| 10,049,346 B2 | 8/2018 | Jensen et al. |
| 10,061,894 B2 | 8/2018 | Sethumadhavan et al. |
| 10,095,649 B2 | 10/2018 | Joshua et al. |
| 10,127,357 B2 | 11/2018 | Whiting et al. |
| 10,152,575 B2 | 12/2018 | Sexton et al. |
| 10,173,008 B2 | 1/2019 | Simpson et al. |
| 10,185,834 B2 | 1/2019 | Adam et al. |
| 10,207,031 B2 | 2/2019 | Toth |
| 10,328,188 B2 | 6/2019 | Deutsch et al. |
| 2002/0087360 A1 | 7/2002 | Pettit |
| 2002/0128804 A1 | 9/2002 | Geva |
| 2002/0128869 A1 | 9/2002 | Kuth |
| 2002/0135336 A1 | 9/2002 | Zhou et al. |
| 2002/0177757 A1 | 11/2002 | Britton |
| 2002/0184055 A1 | 12/2002 | Naghavi et al. |
| 2003/0009244 A1 | 1/2003 | Engleson et al. |
| 2003/0018736 A1 | 1/2003 | Christ et al. |
| 2003/0105649 A1 | 6/2003 | Sheiner et al. |
| 2003/0182158 A1 | 9/2003 | Son |
| 2003/0221687 A1 | 12/2003 | Kaigler |
| 2003/0229518 A1 | 12/2003 | Abraham-Fuchs et al. |
| 2004/0006492 A1 | 1/2004 | Watanabe |
| 2004/0054775 A1 | 3/2004 | Poliac et al. |
| 2004/0078223 A1 | 4/2004 | Sacco et al. |
| 2004/0143458 A1 | 7/2004 | Pulkkinen et al. |
| 2004/0158193 A1* | 8/2004 | Bui ............... A61M 5/172 |
| | | 128/DIG. 13 |
| 2004/0167802 A1 | 8/2004 | Takada et al. |
| 2004/0167804 A1 | 8/2004 | Simpson et al. |
| 2004/0172301 A1 | 9/2004 | Mihai et al. |
| 2004/0181433 A1 | 9/2004 | Blair |
| 2004/0193449 A1 | 9/2004 | Wildman et al. |
| 2004/0204962 A1 | 10/2004 | Howser et al. |
| 2005/0033124 A1 | 2/2005 | Kelly et al. |
| 2005/0055225 A1 | 3/2005 | Mehl |
| 2005/0055242 A1 | 3/2005 | Bello et al. |
| 2005/0055244 A1 | 3/2005 | Mullan et al. |
| 2005/0060211 A1 | 3/2005 | Xiao et al. |
| 2005/0065817 A1 | 3/2005 | Mihai et al. |
| 2005/0097200 A1 | 5/2005 | Denning, Jr. et al. |
| 2005/0102167 A1 | 5/2005 | Kapoor |
| 2005/0108046 A1 | 5/2005 | Craft |
| 2005/0108057 A1 | 5/2005 | Cohen et al. |
| 2005/0114176 A1 | 5/2005 | Dominick et al. |
| 2005/0119914 A1 | 6/2005 | Batch |
| 2005/0222873 A1 | 10/2005 | Nephin et al. |
| 2005/0240111 A1 | 10/2005 | Chung |
| 2005/0283382 A1 | 12/2005 | Donoghue et al. |
| 2006/0004604 A1 | 1/2006 | White |
| 2006/0064323 A1 | 3/2006 | Alleckson et al. |
| 2006/0085393 A1 | 4/2006 | Modesitt |
| 2006/0089539 A1 | 4/2006 | Miodownik et al. |
| 2006/0095853 A1 | 5/2006 | Amyot et al. |
| 2006/0155584 A1 | 7/2006 | Aggarwal |
| 2006/0161460 A1 | 7/2006 | Smitherman et al. |
| 2006/0190130 A1 | 8/2006 | Fedor et al. |
| 2006/0195843 A1 | 8/2006 | Hall |

(56) References Cited

U.S. PATENT DOCUMENTS

| | | |
|---|---|---|
| 2006/0224051 A1 | 10/2006 | Teller et al. |
| 2006/0246922 A1 | 11/2006 | Gasbarro et al. |
| 2007/0136099 A1 | 6/2007 | Neligh et al. |
| 2007/0156456 A1 | 7/2007 | McGillin et al. |
| 2007/0197881 A1 | 8/2007 | Wolf et al. |
| 2007/0219826 A1 | 9/2007 | Brodsky et al. |
| 2007/0255116 A1 | 11/2007 | Mehta et al. |
| 2007/0271298 A1 | 11/2007 | Juang et al. |
| 2008/0009681 A1 | 1/2008 | Al |
| 2008/0086357 A1 | 4/2008 | Choubey et al. |
| 2008/0091659 A1 | 4/2008 | McFaul |
| 2008/0119705 A1 | 5/2008 | Patel et al. |
| 2008/0126126 A1 | 5/2008 | Ballai |
| 2008/0140160 A1 | 6/2008 | Goetz et al. |
| 2008/0167534 A1 | 7/2008 | Young et al. |
| 2008/0177579 A1 | 7/2008 | Dehaan |
| 2008/0221396 A1 | 9/2008 | Garces et al. |
| 2008/0242945 A1 | 10/2008 | Gugliotti et al. |
| 2008/0312953 A1 | 12/2008 | Claus |
| 2009/0037220 A1 | 2/2009 | Chambers et al. |
| 2009/0048492 A1 | 2/2009 | Rantala et al. |
| 2009/0048865 A1 | 2/2009 | Breazeale, Jr. |
| 2009/0097623 A1 | 4/2009 | Bharadwaj |
| 2009/0099866 A1 | 4/2009 | Newman |
| 2009/0099867 A1 | 4/2009 | Newman |
| 2009/0115663 A1 | 5/2009 | Brown et al. |
| 2009/0118591 A1 | 5/2009 | Kim et al. |
| 2009/0125331 A1 | 5/2009 | Pamsgaard et al. |
| 2009/0136909 A1 | 5/2009 | Asukai et al. |
| 2009/0144091 A1 | 6/2009 | Rago |
| 2009/0157429 A1 | 6/2009 | Lee et al. |
| 2009/0163774 A1 | 6/2009 | Thatha et al. |
| 2009/0171166 A1 | 7/2009 | Amundson et al. |
| 2009/0177495 A1 | 7/2009 | Abousy et al. |
| 2009/0187424 A1 | 7/2009 | Grabowski |
| 2009/0204434 A1 | 8/2009 | Breazeale, Jr. |
| 2009/0204435 A1 | 8/2009 | Gale |
| 2009/0205042 A1 | 8/2009 | Zhou et al. |
| 2009/0224889 A1 | 9/2009 | Aggarwal et al. |
| 2009/0270833 A1 | 10/2009 | Debelser et al. |
| 2009/0281822 A1 | 11/2009 | Warner et al. |
| 2009/0281830 A1 | 11/2009 | McNames et al. |
| 2009/0281867 A1 | 11/2009 | Sievenpiper et al. |
| 2009/0326339 A1 | 12/2009 | Horvitz |
| 2009/0327102 A1 | 12/2009 | Maniar et al. |
| 2010/0001838 A1 | 1/2010 | Miodownik et al. |
| 2010/0017471 A1 | 1/2010 | Brown et al. |
| 2010/0022848 A1 | 1/2010 | Lee et al. |
| 2010/0022990 A1 | 1/2010 | Karpowicz et al. |
| 2010/0030302 A1 | 2/2010 | Blowers et al. |
| 2010/0036333 A1 | 2/2010 | Schenk, III et al. |
| 2010/0090004 A1 | 4/2010 | Sands et al. |
| 2010/0106528 A1 | 4/2010 | Brackett et al. |
| 2010/0113908 A1 | 5/2010 | Vargas et al. |
| 2010/0145161 A1 | 6/2010 | Niyato et al. |
| 2010/0222645 A1 | 9/2010 | Nadler et al. |
| 2010/0234708 A1 | 9/2010 | Buck et al. |
| 2010/0255876 A1 | 10/2010 | Jordan et al. |
| 2011/0004188 A1 | 1/2011 | Shekalim |
| 2011/0066110 A1 | 3/2011 | Fathallah et al. |
| 2011/0071844 A1 | 3/2011 | Cannon et al. |
| 2011/0073107 A1 | 3/2011 | Rodman et al. |
| 2011/0077605 A1 | 3/2011 | Karpowicz et al. |
| 2011/0106561 A1 | 5/2011 | Eaton, Jr. et al. |
| 2011/0137759 A1 | 6/2011 | Wellington et al. |
| 2011/0145018 A1 | 6/2011 | Fotsch et al. |
| 2011/0173028 A1 | 7/2011 | Bond |
| 2011/0184754 A1 | 7/2011 | Park et al. |
| 2011/0225008 A1 | 9/2011 | Elkouh et al. |
| 2011/0225499 A1* | 9/2011 | Lu ................... G06F 9/44505 715/735 |
| 2011/0246219 A1 | 10/2011 | Smith et al. |
| 2011/0275353 A1 | 11/2011 | Liu |
| 2011/0288878 A1 | 11/2011 | Blair |
| 2012/0029312 A1 | 2/2012 | Beaudry et al. |
| 2012/0029313 A1 | 2/2012 | Burdett et al. |
| 2012/0032819 A1 | 2/2012 | Chae et al. |
| 2012/0035427 A1 | 2/2012 | Friedman et al. |
| 2012/0077605 A1 | 3/2012 | Nakagaito et al. |
| 2012/0081225 A1 | 4/2012 | Waugh et al. |
| 2012/0089369 A1 | 4/2012 | Abuzeni et al. |
| 2012/0123323 A1 | 5/2012 | Kagan et al. |
| 2012/0123796 A1 | 5/2012 | McFaul |
| 2012/0157889 A1 | 6/2012 | Tanis et al. |
| 2012/0181405 A1 | 7/2012 | Zlatic et al. |
| 2012/0182143 A1 | 7/2012 | Gaines et al. |
| 2012/0191475 A1 | 7/2012 | Pandey |
| 2012/0212455 A1 | 8/2012 | Kloeffel |
| 2012/0215455 A1 | 8/2012 | Patil et al. |
| 2012/0259651 A1 | 10/2012 | Mallon et al. |
| 2012/0271256 A1 | 10/2012 | Locke et al. |
| 2012/0290217 A1 | 11/2012 | Shoval et al. |
| 2012/0295566 A1 | 11/2012 | Collins et al. |
| 2012/0310205 A1 | 12/2012 | Lee et al. |
| 2013/0018355 A1 | 1/2013 | Brand et al. |
| 2013/0035615 A1 | 2/2013 | Hsieh |
| 2013/0045764 A1 | 2/2013 | Vik et al. |
| 2013/0073303 A1 | 3/2013 | Hsu |
| 2013/0076528 A1 | 3/2013 | Boettner et al. |
| 2013/0087609 A1 | 4/2013 | Nichol et al. |
| 2013/0090949 A1 | 4/2013 | Tibebu |
| 2013/0103419 A1 | 4/2013 | Beaudry |
| 2013/0124227 A1 | 5/2013 | Ellis |
| 2013/0132855 A1 | 5/2013 | Manicka et al. |
| 2013/0150686 A1 | 6/2013 | Fronterhouse et al. |
| 2013/0150698 A1 | 6/2013 | Hsu et al. |
| 2013/0151274 A1 | 6/2013 | Bage et al. |
| 2013/0157571 A1 | 6/2013 | Wondka et al. |
| 2013/0159456 A1 | 6/2013 | Daoud et al. |
| 2013/0160082 A1 | 6/2013 | Miller |
| 2013/0186405 A1 | 7/2013 | Krzyzanowski et al. |
| 2013/0190903 A1 | 7/2013 | Balakrishnan et al. |
| 2013/0191513 A1 | 7/2013 | Kamen et al. |
| 2013/0196703 A1 | 8/2013 | Masoud et al. |
| 2013/0204106 A1 | 8/2013 | Bennett |
| 2013/0211206 A1 | 8/2013 | Sands et al. |
| 2013/0211854 A1 | 8/2013 | Wagstaff |
| 2013/0212168 A1 | 8/2013 | Bonasera et al. |
| 2013/0214925 A1 | 8/2013 | Weiss |
| 2013/0218053 A1 | 8/2013 | Kaiser et al. |
| 2013/0226607 A1 | 8/2013 | Woody et al. |
| 2013/0227128 A1 | 8/2013 | Wagstaff |
| 2013/0231596 A1 | 9/2013 | Hornbach et al. |
| 2013/0245387 A1 | 9/2013 | Patel |
| 2013/0253952 A1 | 9/2013 | Burke et al. |
| 2013/0255681 A1 | 10/2013 | Batch et al. |
| 2013/0267919 A1 | 10/2013 | Caso et al. |
| 2013/0268283 A1 | 10/2013 | Vann et al. |
| 2013/0271556 A1 | 10/2013 | Ross et al. |
| 2013/0282395 A1 | 10/2013 | Rustgi et al. |
| 2013/0285837 A1 | 10/2013 | Uchida |
| 2013/0297350 A1 | 11/2013 | Gross et al. |
| 2013/0304489 A1 | 11/2013 | Miller |
| 2013/0310726 A1 | 11/2013 | Miller et al. |
| 2013/0317753 A1 | 11/2013 | Kamen et al. |
| 2013/0325508 A1 | 12/2013 | Johnson et al. |
| 2013/0331748 A1 | 12/2013 | Wright et al. |
| 2013/0332197 A1 | 12/2013 | Hinkel |
| 2013/0335233 A1 | 12/2013 | Kamar et al. |
| 2013/0339049 A1 | 12/2013 | Blumberg, Jr. et al. |
| 2013/0345524 A1 | 12/2013 | Meyer et al. |
| 2014/0002234 A1 | 1/2014 | Alwan |
| 2014/0005618 A1 | 1/2014 | Locke et al. |
| 2014/0028464 A1 | 1/2014 | Garibaldi |
| 2014/0031884 A1 | 1/2014 | Elghazzawi |
| 2014/0032231 A1 | 1/2014 | Semen et al. |
| 2014/0058714 A1 | 2/2014 | Boyer |
| 2014/0087762 A1 | 3/2014 | Galvin et al. |
| 2014/0108033 A1 | 4/2014 | Akbay et al. |
| 2014/0108034 A1 | 4/2014 | Akbay et al. |
| 2014/0108035 A1 | 4/2014 | Akbay et al. |
| 2014/0129250 A1 | 5/2014 | Daniel et al. |
| 2014/0148138 A1 | 5/2014 | Chou |

(56) References Cited

U.S. PATENT DOCUMENTS

| | | | |
|---|---|---|---|
| 2014/0163919 A1* | 6/2014 | Manigel | A61M 5/168 |
| | | | 702/123 |
| 2014/0171753 A1 | 6/2014 | Montejo et al. | |
| 2014/0187888 A1 | 7/2014 | Hatziantoniou | |
| 2014/0207090 A1 | 7/2014 | Jian | |
| 2014/0222446 A1 | 8/2014 | Ash et al. | |
| 2014/0235975 A1 | 8/2014 | Carnes | |
| 2014/0244285 A1 | 8/2014 | Hinkle et al. | |
| 2014/0244301 A1 | 8/2014 | Lee et al. | |
| 2014/0244307 A1 | 8/2014 | Shutko et al. | |
| 2014/0266713 A1 | 9/2014 | Sehgal et al. | |
| 2014/0275876 A1 | 9/2014 | Hansen et al. | |
| 2014/0278502 A1 | 9/2014 | Laskin | |
| 2014/0280882 A1 | 9/2014 | Lacerte et al. | |
| 2014/0297299 A1 | 10/2014 | Lester, IV | |
| 2014/0316819 A1 | 10/2014 | Dunsirn et al. | |
| 2014/0350966 A1 | 11/2014 | Khatana et al. | |
| 2014/0366878 A1 | 12/2014 | Baron | |
| 2014/0372147 A1 | 12/2014 | White | |
| 2014/0372522 A1 | 12/2014 | Orona et al. | |
| 2014/0375470 A1 | 12/2014 | Malveaux | |
| 2014/0378895 A1 | 12/2014 | Barack | |
| 2015/0012290 A1 | 1/2015 | Inciardi et al. | |
| 2015/0019237 A1 | 1/2015 | Doyle et al. | |
| 2015/0019257 A1 | 1/2015 | Doyle et al. | |
| 2015/0025486 A1 | 1/2015 | Hu et al. | |
| 2015/0046137 A1 | 2/2015 | Zeilinger | |
| 2015/0066531 A1 | 3/2015 | Jacobson et al. | |
| 2015/0072613 A1 | 3/2015 | Swanson | |
| 2015/0094830 A1 | 4/2015 | Lipoma et al. | |
| 2015/0095056 A1 | 4/2015 | Ryan et al. | |
| 2015/0095059 A1 | 4/2015 | Yegge et al. | |
| 2015/0095066 A1 | 4/2015 | Ryan et al. | |
| 2015/0095068 A1 | 4/2015 | Ryan et al. | |
| 2015/0100340 A1 | 4/2015 | Folsom et al. | |
| 2015/0112707 A1 | 4/2015 | Manice et al. | |
| 2015/0118662 A1 | 4/2015 | Ellison et al. | |
| 2015/0119652 A1 | 4/2015 | Hyde et al. | |
| 2015/0120318 A1 | 4/2015 | Toyama | |
| 2015/0133829 A1* | 5/2015 | DeBusk | A61M 1/743 |
| | | | 601/6 |
| 2015/0143300 A1 | 5/2015 | Zhang et al. | |
| 2015/0164323 A1 | 6/2015 | Holtzclaw | |
| 2015/0164376 A1 | 6/2015 | Huang | |
| 2015/0186615 A1 | 7/2015 | Armor et al. | |
| 2015/0189001 A1 | 7/2015 | Lee et al. | |
| 2015/0227716 A1 | 8/2015 | Ryan et al. | |
| 2015/0227717 A1 | 8/2015 | Ryan et al. | |
| 2015/0234557 A1 | 8/2015 | Dorn | |
| 2015/0234995 A1 | 8/2015 | Casady et al. | |
| 2015/0242578 A1 | 8/2015 | Siemon | |
| 2015/0242583 A1 | 8/2015 | Edson | |
| 2015/0254403 A1 | 9/2015 | Laperna | |
| 2015/0257643 A1 | 9/2015 | Watson et al. | |
| 2015/0261920 A1 | 9/2015 | Blick | |
| 2015/0269323 A1 | 9/2015 | Ginsburg | |
| 2015/0286970 A1 | 10/2015 | Dickerson et al. | |
| 2015/0304478 A1 | 10/2015 | Kim et al. | |
| 2015/0310182 A1 | 10/2015 | Henze et al. | |
| 2015/0324943 A1 | 11/2015 | Han et al. | |
| 2015/0339445 A1 | 11/2015 | Gruby et al. | |
| 2015/0343188 A1* | 12/2015 | Allan | A61M 1/90 |
| | | | 604/292 |
| 2015/0363058 A1 | 12/2015 | Chung et al. | |
| 2015/0370984 A1 | 12/2015 | Russell et al. | |
| 2015/0370997 A1 | 12/2015 | Krongrad et al. | |
| 2015/0379441 A1 | 12/2015 | Syed et al. | |
| 2016/0004824 A1 | 1/2016 | Stanton et al. | |
| 2016/0018963 A1 | 1/2016 | Robbins et al. | |
| 2016/0042154 A1 | 2/2016 | Goldberg et al. | |
| 2016/0044141 A1 | 2/2016 | Pfützenreuter et al. | |
| 2016/0055310 A1 | 2/2016 | Bentley et al. | |
| 2016/0058286 A1 | 3/2016 | Joshua et al. | |
| 2016/0063210 A1 | 3/2016 | Bardi et al. | |
| 2016/0066864 A1 | 3/2016 | Frieder et al. | |
| 2016/0080365 A1 | 3/2016 | Baker et al. | |
| 2016/0085415 A1 | 3/2016 | Humphrys et al. | |
| 2016/0098524 A1 | 4/2016 | Himmelstein | |
| 2016/0110507 A1 | 4/2016 | Abbo | |
| 2016/0128571 A1 | 5/2016 | Adler | |
| 2016/0129186 A1 | 5/2016 | Douglas et al. | |
| 2016/0135752 A1 | 5/2016 | Beaumont | |
| 2016/0142443 A1 | 5/2016 | Ting et al. | |
| 2016/0151015 A1 | 6/2016 | Condurso et al. | |
| 2016/0154936 A1 | 6/2016 | Kalathil | |
| 2016/0154943 A1 | 6/2016 | Cho et al. | |
| 2016/0171866 A1 | 6/2016 | Dupasquier et al. | |
| 2016/0180031 A1 | 6/2016 | Slater | |
| 2016/0184497 A1 | 6/2016 | Phillips et al. | |
| 2016/0196399 A1 | 7/2016 | Bonhomme | |
| 2016/0203275 A1 | 7/2016 | Benjamin et al. | |
| 2016/0203283 A1 | 7/2016 | Baruah et al. | |
| 2016/0209837 A1 | 7/2016 | Kim | |
| 2016/0212577 A1 | 7/2016 | Dor et al. | |
| 2016/0217433 A1 | 7/2016 | Walton et al. | |
| 2016/0246943 A1 | 8/2016 | Lake et al. | |
| 2016/0260035 A1 | 9/2016 | Crooks et al. | |
| 2016/0287189 A1 | 10/2016 | Modai et al. | |
| 2016/0308969 A1 | 10/2016 | Aihara et al. | |
| 2016/0321404 A1 | 11/2016 | Ginsburg | |
| 2016/0321422 A1 | 11/2016 | Albright | |
| 2017/0007494 A1 | 1/2017 | Rock et al. | |
| 2017/0014028 A1 | 1/2017 | Clear, Jr. | |
| 2017/0017765 A1 | 1/2017 | Yegge et al. | |
| 2017/0032648 A1 | 2/2017 | McClain et al. | |
| 2017/0046503 A1 | 2/2017 | Cho et al. | |
| 2017/0053073 A1 | 2/2017 | Allen et al. | |
| 2017/0055205 A1 | 2/2017 | Morris et al. | |
| 2017/0068781 A1 | 3/2017 | Zasowski et al. | |
| 2017/0074717 A1 | 3/2017 | Pilkington et al. | |
| 2017/0078396 A1 | 3/2017 | Haas et al. | |
| 2017/0116373 A1 | 4/2017 | Ginsburg et al. | |
| 2017/0140120 A1 | 5/2017 | Thrower | |
| 2017/0150939 A1 | 6/2017 | Shah | |
| 2017/0193181 A1 | 7/2017 | Carter et al. | |
| 2017/0212995 A1 | 7/2017 | Ingmanson | |
| 2017/0257682 A1 | 9/2017 | Shtalryd | |
| 2017/0270533 A1 | 9/2017 | Barton et al. | |
| 2017/0273116 A1 | 9/2017 | Elghazzawi | |
| 2017/0327371 A1 | 11/2017 | Bai et al. | |
| 2017/0372010 A1 | 12/2017 | Doherty et al. | |
| 2018/0004908 A1 | 1/2018 | Barrus et al. | |
| 2018/0052454 A1 | 2/2018 | Magno et al. | |
| 2018/0121629 A1 | 5/2018 | Dyer et al. | |
| 2018/0139572 A1 | 5/2018 | Hansen | |
| 2018/0144817 A1 | 5/2018 | Lofgren et al. | |
| 2018/0158545 A1 | 6/2018 | Blomquist | |
| 2018/0160907 A1 | 6/2018 | Verma | |
| 2018/0181714 A1 | 6/2018 | Pillarisetty et al. | |
| 2018/0233016 A1 | 8/2018 | Daniel et al. | |
| 2018/0233221 A1 | 8/2018 | Blomquist | |
| 2018/0279880 A1 | 10/2018 | Bacchi | |
| 2018/0286502 A1 | 10/2018 | Lane et al. | |
| 2018/0308569 A1 | 10/2018 | Luellen | |
| 2018/0308573 A1 | 10/2018 | Hochrein et al. | |
| 2018/0315492 A1 | 11/2018 | Bishop et al. | |
| 2018/0322944 A1 | 11/2018 | Valdizan | |

FOREIGN PATENT DOCUMENTS

| | | |
|---|---|---|
| DE | 102010036405 A1 | 1/2012 |
| EP | 0980227 A1 | 2/2000 |
| EP | 0566381 B1 | 7/2002 |
| EP | 1231965 A2 | 8/2002 |
| EP | 1291802 A2 | 3/2003 |
| EP | 1309960 A1 | 5/2003 |
| EP | 0814864 B1 | 12/2003 |
| EP | 1407624 A2 | 4/2004 |
| EP | 1011420 B1 | 12/2004 |
| EP | 1495713 A1 | 1/2005 |
| EP | 1524619 A2 | 4/2005 |
| EP | 1540557 A2 | 6/2005 |
| EP | 1579367 A2 | 9/2005 |
| EP | 1587017 A2 | 10/2005 |

(56) References Cited

FOREIGN PATENT DOCUMENTS

| | | | |
|---|---|---|---|
| EP | 1788503 | A2 | 5/2007 |
| EP | 1839244 | A1 | 10/2007 |
| EP | 1839615 | A1 | 10/2007 |
| EP | 1857950 | A2 | 11/2007 |
| EP | 1870068 | A1 | 12/2007 |
| EP | 1904964 | A1 | 4/2008 |
| EP | 1934852 | A1 | 6/2008 |
| EP | 1975828 | A2 | 10/2008 |
| EP | 1993435 | A2 | 11/2008 |
| EP | 2038786 | A2 | 3/2009 |
| EP | 2040604 | A2 | 4/2009 |
| EP | 2092470 | A2 | 8/2009 |
| EP | 2146297 | A1 | 1/2010 |
| EP | 2172859 | A1 | 4/2010 |
| EP | 2214552 | A1 | 8/2010 |
| EP | 2218478 | A1 | 8/2010 |
| EP | 1404213 | B1 | 3/2011 |
| EP | 1247229 | B1 | 4/2011 |
| EP | 1406540 | B1 | 6/2011 |
| EP | 1812094 | B1 | 8/2011 |
| EP | 2384472 | A1 | 11/2011 |
| EP | 2226002 | B1 | 1/2012 |
| EP | 1610494 | B1 | 3/2012 |
| EP | 1248660 | B1 | 4/2012 |
| EP | 2023800 | B1 | 4/2012 |
| EP | 2451513 | A1 | 5/2012 |
| EP | 1248661 | B1 | 8/2012 |
| EP | 2488977 | A1 | 8/2012 |
| EP | 2562665 | A2 | 2/2013 |
| EP | 2619723 | A2 | 7/2013 |
| EP | 1881784 | B1 | 10/2013 |
| EP | 2664194 | A2 | 11/2013 |
| EP | 2743850 | A2 | 6/2014 |
| EP | 2745204 | A1 | 6/2014 |
| EP | 1684146 | B1 | 7/2014 |
| EP | 2795492 | A1 | 10/2014 |
| EP | 2841895 | A1 | 3/2015 |
| EP | 2850771 | A1 | 3/2015 |
| EP | 2876567 | A1 | 5/2015 |
| EP | 2891999 | A2 | 7/2015 |
| EP | 2894581 | A1 | 7/2015 |
| EP | 2906101 | A2 | 8/2015 |
| EP | 2945084 | A1 | 11/2015 |
| EP | 2962266 | A1 | 1/2016 |
| EP | 2968829 | A1 | 1/2016 |
| EP | 2973089 | A1 | 1/2016 |
| EP | 3000082 | A1 | 3/2016 |
| EP | 3010398 | A1 | 4/2016 |
| EP | 3054389 | A2 | 8/2016 |
| EP | 3070628 | A1 | 9/2016 |
| EP | 3078010 | A1 | 10/2016 |
| EP | 3096113 | A1 | 11/2016 |
| EP | 2563437 | B1 | 3/2017 |
| EP | 2773393 | B1 | 3/2017 |
| EP | 3134854 | A1 | 3/2017 |
| EP | 3027242 | B1 | 4/2017 |
| EP | 2556650 | B1 | 5/2017 |
| EP | 3174569 | A1 | 6/2017 |
| EP | 2632407 | B1 | 8/2017 |
| EP | 3209358 | A1 | 8/2017 |
| EP | 3041571 | B1 | 9/2017 |
| EP | 2856767 | B1 | 11/2017 |
| EP | 3252635 | A1 | 12/2017 |
| EP | 2320971 | B1 | 5/2018 |
| EP | 2335173 | B1 | 5/2018 |
| EP | 3100188 | B1 | 6/2018 |
| EP | 3330973 | A1 | 6/2018 |
| EP | 3352174 | A1 | 7/2018 |
| EP | 2440112 | B1 | 10/2018 |
| EP | 3400549 | A1 | 11/2018 |
| EP | 2992500 | B1 | 12/2018 |
| EP | 2597584 | B1 | 1/2019 |
| EP | 3219340 | B1 | 1/2019 |
| EP | 2890456 | B1 | 2/2019 |
| EP | 3377130 | B1 | 4/2019 |
| EP | 2881875 | B1 | 5/2019 |
| EP | 2836269 | B1 | 8/2019 |
| GB | 2409951 | A | 7/2005 |
| GB | 2436160 | A | 9/2007 |
| GB | 2449400 | A | 11/2008 |
| GB | 2456708 | A | 7/2009 |
| GB | 2423178 | B | 5/2010 |
| GB | 2475091 | A | 5/2011 |
| GB | 2488904 | A | 9/2012 |
| GB | 2446923 | B | 5/2013 |
| GB | 2499986 | A | 9/2013 |
| GB | 2491946 | B | 8/2014 |
| GB | 2499873 | B | 5/2016 |
| GB | 2533910 | A | 7/2016 |
| GB | 2541286 | A | 2/2017 |
| GB | 2550576 | B | 6/2018 |
| WO | WO 96/27163 | A1 | 9/1996 |
| WO | WO 97/44745 | A1 | 11/1997 |
| WO | WO 99/24927 | A1 | 5/1999 |
| WO | WO 99/63886 | A1 | 12/1999 |
| WO | WO 00/32088 | A1 | 6/2000 |
| WO | WO 00/60522 | A2 | 10/2000 |
| WO | WO 01/33457 | A1 | 5/2001 |
| WO | WO 01/81829 | A1 | 11/2001 |
| WO | WO 02/17075 | A2 | 2/2002 |
| WO | WO 02/33577 | A1 | 4/2002 |
| WO | WO 02/078594 | A2 | 10/2002 |
| WO | WO 02/101713 | A1 | 12/2002 |
| WO | WO 03/054668 | A2 | 7/2003 |
| WO | WO 2004/057514 | A2 | 7/2004 |
| WO | WO 2004/074457 | A2 | 9/2004 |
| WO | WO 2005/022349 | A2 | 3/2005 |
| WO | WO 2005/031632 | A2 | 4/2005 |
| WO | WO 2005/036447 | A2 | 4/2005 |
| WO | WO 2005/045461 | A1 | 5/2005 |
| WO | WO 2005/053793 | A1 | 6/2005 |
| WO | WO 2005/057466 | A2 | 6/2005 |
| WO | WO 2005/083619 | A2 | 9/2005 |
| WO | WO 2005/101282 | A2 | 10/2005 |
| WO | WO 2005/109297 | A2 | 11/2005 |
| WO | WO 2005/120097 | A2 | 12/2005 |
| WO | WO 2006/021154 | A1 | 3/2006 |
| WO | WO 2006/066583 | A1 | 6/2006 |
| WO | WO 2006/066585 | A2 | 6/2006 |
| WO | WO 2006/071711 | A2 | 7/2006 |
| WO | WO 2006/099120 | A2 | 9/2006 |
| WO | WO 2006/108304 | A1 | 10/2006 |
| WO | WO 2006/108858 | A1 | 10/2006 |
| WO | WO 2006/111109 | A1 | 10/2006 |
| WO | WO 2007/027490 | A2 | 3/2007 |
| WO | WO 2007/035646 | A2 | 3/2007 |
| WO | WO 2007/127879 | A2 | 11/2007 |
| WO | WO 2007/133478 | A2 | 11/2007 |
| WO | WO 2007/137869 | A2 | 12/2007 |
| WO | WO 2008/010012 | A2 | 1/2008 |
| WO | WO 2008/036344 | A1 | 3/2008 |
| WO | WO 2008/062382 | A2 | 5/2008 |
| WO | WO 2008/116295 | A1 | 10/2008 |
| WO | WO 2008/150633 | A2 | 12/2008 |
| WO | WO 2009/140669 | A2 | 11/2009 |
| WO | WO 2010/017484 | A2 | 2/2010 |
| WO | WO 2010/025166 | A1 | 3/2010 |
| WO | WO 2010/025467 | A1 | 3/2010 |
| WO | WO 2010/078558 | A1 | 7/2010 |
| WO | WO 2010/085033 | A2 | 7/2010 |
| WO | WO 2010/132617 | A2 | 11/2010 |
| WO | WO 2010/145780 | A1 | 12/2010 |
| WO | WO 2011/005633 | A2 | 1/2011 |
| WO | WO 2011/023384 | A1 | 3/2011 |
| WO | WO 2011/039676 | A2 | 4/2011 |
| WO | WO 2011/046860 | A2 | 4/2011 |
| WO | WO 2011/047334 | A1 | 4/2011 |
| WO | WO 2011/123933 | A1 | 10/2011 |
| WO | WO 2011/137230 | A1 | 11/2011 |
| WO | WO 2012/051278 | A1 | 4/2012 |
| WO | WO 2012/127281 | A1 | 9/2012 |
| WO | WO 2013/026999 | A1 | 2/2013 |
| WO | WO 2013/036853 | A2 | 3/2013 |
| WO | WO 2013/061887 | A1 | 5/2013 |

(56) References Cited

FOREIGN PATENT DOCUMENTS

| | | |
|---|---|---|
| WO | WO 2013/102855 A1 | 7/2013 |
| WO | WO 2013/109517 A1 | 7/2013 |
| WO | WO 2013/138182 A1 | 9/2013 |
| WO | WO 2013/141870 A1 | 9/2013 |
| WO | WO 2013/155193 A1 | 10/2013 |
| WO | WO 2013/175076 A1 | 11/2013 |
| WO | WO 2014/015215 A2 | 1/2014 |
| WO | WO 2014/018786 A2 | 1/2014 |
| WO | WO 2014/075494 A1 | 5/2014 |
| WO | WO 2014/089086 A1 | 6/2014 |
| WO | WO 2014/100036 A1 | 6/2014 |
| WO | WO 2014/100687 A2 | 6/2014 |
| WO | WO 2014/106056 A2 | 7/2014 |
| WO | WO 2014/123846 A1 | 8/2014 |
| WO | WO 2014/133822 A2 | 9/2014 |
| WO | WO 2014/141221 A2 | 9/2014 |
| WO | WO 2014/145496 A1 | 9/2014 |
| WO | WO 2014/150255 A2 | 9/2014 |
| WO | WO 2014/152963 A1 | 9/2014 |
| WO | WO 2014/189070 A1 | 11/2014 |
| WO | WO 2014/009876 A3 | 12/2014 |
| WO | WO 2015/019273 A2 | 2/2015 |
| WO | WO 2015/025482 A1 | 2/2015 |
| WO | WO 2015/026387 A1 | 2/2015 |
| WO | WO 2015/050816 A1 | 4/2015 |
| WO | WO 2015/078112 A1 | 6/2015 |
| WO | WO 2015/085249 A1 | 6/2015 |
| WO | WO 2015/091070 A1 | 6/2015 |
| WO | WO 2015/124670 A1 | 8/2015 |
| WO | WO 2015/132528 A1 | 9/2015 |
| WO | WO 2015/140801 A2 | 9/2015 |
| WO | WO 2015/143099 A2 | 9/2015 |
| WO | WO 2015/145455 A1 | 10/2015 |
| WO | WO 2015/156143 A1 | 10/2015 |
| WO | WO 2015/164787 A1 | 10/2015 |
| WO | WO 2015/179915 A1 | 12/2015 |
| WO | WO 2015/179916 A1 | 12/2015 |
| WO | WO 2015/179917 A1 | 12/2015 |
| WO | WO 2015/181836 A2 | 12/2015 |
| WO | WO 2015/187480 A1 | 12/2015 |
| WO | WO 2016/001088 A1 | 1/2016 |
| WO | WO 2016/006536 A1 | 1/2016 |
| WO | WO 2016/019191 | 2/2016 |
| WO | WO 2016/075656 A1 | 5/2016 |
| WO | WO 2016/108163 A1 | 7/2016 |
| WO | WO 2016/118318 A1 | 7/2016 |
| WO | WO 2016/120820 A2 | 8/2016 |
| WO | WO 2016/136694 A1 | 9/2016 |
| WO | WO 2016/141799 A1 | 9/2016 |
| WO | WO 2016/151364 A1 | 9/2016 |
| WO | WO 2016/160849 A1 | 10/2016 |
| WO | WO 2016/175649 A1 | 11/2016 |
| WO | WO 2016/178936 A1 | 11/2016 |
| WO | WO 2016/190978 A1 | 12/2016 |
| WO | WO 2017/001848 A1 | 1/2017 |
| WO | WO 2017/004423 A1 | 1/2017 |
| WO | WO 2017/027729 A2 | 2/2017 |
| WO | WO 2017/035024 A1 | 3/2017 |
| WO | WO 2017/053384 A1 | 3/2017 |
| WO | WO 2017/062042 A1 | 4/2017 |
| WO | WO 2017/142100 A1 | 8/2017 |
| WO | WO 2017/165895 A1 | 9/2017 |
| WO | WO 2017/192673 A1 | 11/2017 |
| WO | WO 2018/007100 A1 | 1/2018 |
| WO | WO 2018/013666 A1 | 1/2018 |
| WO | WO 2018/033819 A1 | 2/2018 |
| WO | WO 2018/044894 A1 | 3/2018 |
| WO | WO 2018/064234 A1 | 4/2018 |
| WO | WO 2018/067593 A2 | 4/2018 |
| WO | WO 2018/082813 A1 | 5/2018 |
| WO | WO 2018/091492 A1 | 5/2018 |
| WO | WO 2018/096390 A1 | 5/2018 |
| WO | WO 2018/145880 A1 | 8/2018 |
| WO | WO 2019/014141 | 1/2019 |

OTHER PUBLICATIONS

Cinterion., "Cinterion PHS8-P 3G HSPA+," retrieved from http://www.cinterion.com/tl_files/cinterion/downloads/cinterion_datasheet_PHSS_web.pdf, 2012, 2 pages.

International Preliminary Report on Patentability for Application No. PCT/US2018/041313, dated Jan. 23, 2020, 9 pages.

U.S. Appl. No. 60/845,993, filed Sep. 19, 2006, 438 pages.

\* cited by examiner

SYSTEMS AND METHODS FOR DIRECTLY INTERACTING WITH COMMUNICATIONS MODULE OF WOUND THERAPY APPARATUS

CROSS-REFERENCE TO RELATED APPLICATIONS

This application is a U.S. national stage application of International Patent Application No. PCT/US2018/041313, filed Jul. 9, 2018, which claims the benefit of U.S. Provisional Application No. 62/530,480, filed Jul. 10, 2017; the disclosure of which is hereby incorporated by reference in its entirety.

BACKGROUND

Embodiments of the present disclosure relate to methods and apparatuses for dressing and treating a wound with negative or reduced pressure therapy or topical negative pressure (TNP) therapy. In particular, but without limitation, embodiments disclosed herein relate to negative pressure therapy devices, methods for controlling the operation of TNP systems, and methods of using TNP systems.

SUMMARY

In some embodiments, an apparatus for applying negative pressure to a wound is disclosed. The apparatus can include a housing, a pressure source, a first circuit board assembly, and a second circuit board assembly. The pressure source can be at least partially enclosed by the housing and provide negative pressure via a fluid flow path to a wound dressing. The first circuit board assembly can be at least partially enclosed by the housing and include a first controller configured to control a wound therapy with the wound dressing by activation and deactivation of the pressure source. The second circuit board assembly can be at least partially enclosed by the housing and in communication with the first circuit board assembly. The second circuit board assembly can be separate from the first circuit board assembly and include a second controller. The second controller can: communicate therapy data via a communication network, the therapy data being indicative of a characteristic of the wound therapy, receive an executable command from an electronic device, and execute the executable command without providing the executable command to the first controller.

The apparatus of the preceding paragraph can include one or more of the following features: The second controller can receive the executable command from the electronic device via a serial bus electrically connecting the second circuit board assembly and the electronic device. The second controller can receive the executable command from the electronic device via wireless communication. The second controller can wirelessly communicate the therapy data via the communication network. The electronic device may not be supported by the housing. The second controller can receive and execute the executable command without the wound therapy being interrupted. The second controller can receive and execute the executable command to test an operation of the second controller. The second controller can receive and execute the executable command despite the first controller not being operational. The executable command can be a request for hardware or software version data, and execution of the executable command by the second controller can cause the second controller to transmit the hardware or software version data to the electronic device. Execution of the executable command by the second controller can cause the second controller to change a setting associated with operation of the second controller. Execution of the executable command by the second controller can cause the second controller to communicate the therapy data via another communication network rather than the communication network. Execution of the executable command by the second controller can cause the second controller to perform an operation associated with the communication network. The executable command can be an attention (AT) command. The executable command can be a command of a Hayes command set. The second circuit board assembly can include a modem that includes the second controller. The apparatus can further include a third circuit board assembly including a connector interface, and the first hardware controller can receive another executable command via the connector interface from the electronic device. The second hardware controller can receive another executable command from the first hardware controller. The second hardware controller can enter (i) a data mode in which the data processed by the second hardware controller is not executed and (ii) a command mode in which data processed by the second hardware controller is executed. The first controller can gather the therapy data and provide the therapy data to the second controller for transmission. The second controller can receive another executable command from the electronic device and provide the another executable command to the first controller for execution.

In some embodiments, a method is disclosed for operating a wound therapy device that includes a first circuit board assembly and a second circuit board assembly separate from the first circuit board assembly. The method can include, by a first controller mounted to the first circuit board assembly, controlling application of negative pressure with a pressure source to a wound dressing. In addition, the method can include by a second controller mounted to the second circuit board assembly: communicating therapy data via a communication network, the therapy data being indicative of a characteristic of wound therapy performed with the pressure source, receiving an executable command from an electronic device, and executing the executable command without processing the executable command with the first controller.

The method of the preceding paragraph can include one or more of the following features: The receiving can include receiving the executable command from the electronic device via a serial bus electrically connecting the second circuit board assembly and the electronic device. The receiving can include receiving the executable command from the electronic device via wireless communication. The communicating can include wirelessly communicating the therapy data via the communication network. The receiving and executing can include receiving and executing the executable command without the wound therapy being interrupted. The executing can include executing the executable command to test an operation of the second controller. The receiving and executing can include receiving and executing the executable command despite the first controller not being operational. The executable command can be a request for hardware or software version data, and the executing can cause the second controller to transmit the hardware or software version data to the electronic device. The executing can cause the second controller to change a setting associated with operation of the second controller. The executing can cause the second controller to communicate the therapy data via another communication network rather than the communication network.

BRIEF DESCRIPTION OF THE DRAWINGS

Features and advantages of the present disclosure will be apparent from the following detailed description, taken in conjunction with the accompanying drawings of which.

DETAILED DESCRIPTION

Figure 1:
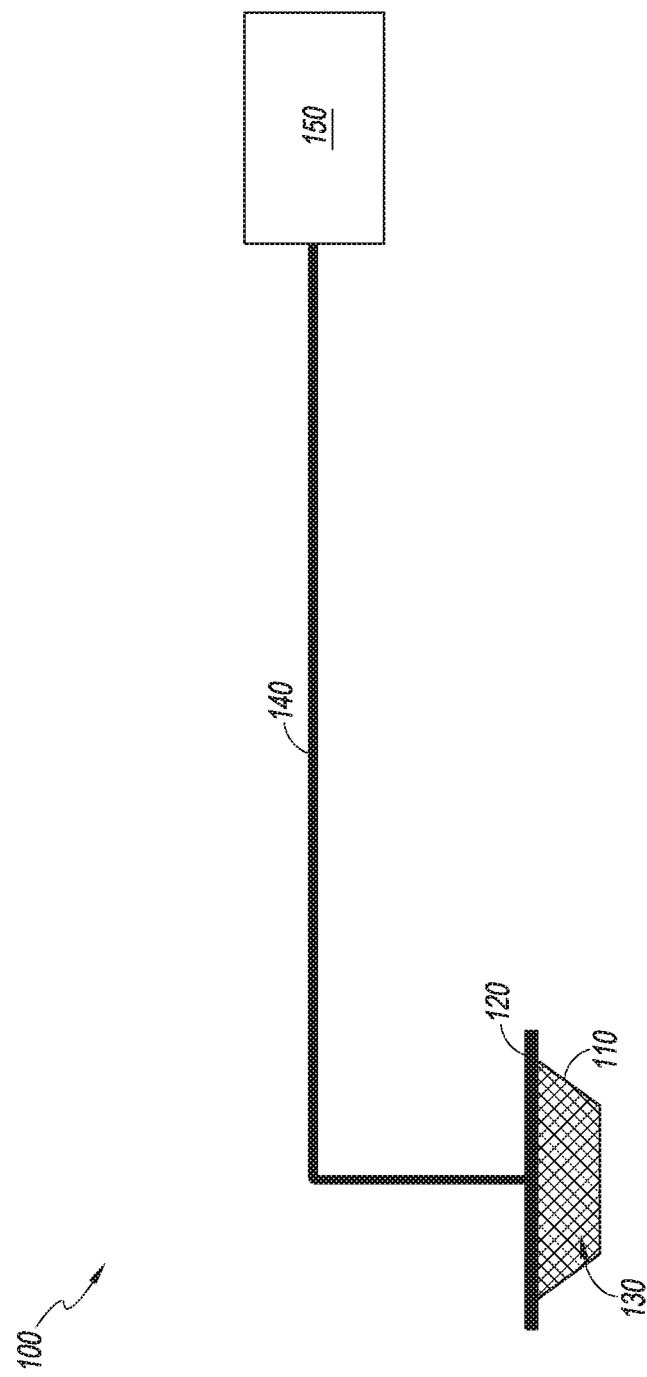
FIG. 1 illustrates a reduced pressure wound therapy system according to some embodiments.

The present disclosure relates to methods and apparatuses for dressing and treating a wound with reduced pressure therapy or topical negative pressure (TNP) therapy. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below.

Many different types of wound dressings are known for aiding in the healing process of a human or animal. These different types of wound dressings include many different types of materials and layers, for example, gauze, pads, foam pads or multi-layer wound dressings. TNP therapy, sometimes referred to as vacuum assisted closure, negative pressure wound therapy, or reduced pressure wound therapy, can be a beneficial mechanism for improving the healing rate of a wound. Such therapy is applicable to a broad range of wounds such as incisional wounds, open wounds and abdominal wounds or the like.

TNP therapy can assist in the closure and healing of wounds by reducing tissue oedema, encouraging blood flow, stimulating the formation of granulation tissue, removing excess exudates, and reducing bacterial load and thus, infection to the wound. Furthermore, TNP therapy can permit less outside disturbance of the wound and promote more rapid healing.

As is used herein, reduced or negative pressure levels, such as −X mmHg, represent pressure levels that are below atmospheric pressure, which typically corresponds to 760 mmHg (or 1 atm, 29.93 inHg, 101.325 kPa, 14.696 psi, etc.). Accordingly, a negative pressure value of −X mmHg reflects pressure that is X mmHg below atmospheric pressure, such as a pressure of (760−X) mmHg. In addition, negative pressure that is "less" or "smaller" than −X mmHg corresponds to pressure that is closer to atmospheric pressure (for example, −40 mmHg is less than −60 mmHg). Negative pressure that is "more" or "greater" than −X mmHg corresponds to pressure that is further from atmospheric pressure (for example, −80 mmHg is more than −60 mmHg).

INTRODUCTION

A pump assembly of a TNP system can include multiple controllers or processors used to control the various operations of the pump assembly. A main controller can, for example, be used to orchestrate an overall functioning of the pump assembly, and one or more other controllers can be used to control one or more specialized functions of the pump assembly (such as communications, negative pressure control, or user interface operations) under direction from the main controller.

A pump assembly can communicate with an electronic device that is separate from the pump assembly by having a main controller of the pump assembly exchange messages with the electronic device. The electronic device may, for instance, transmit an executable command as part of a message to the main controller. The main controller can then receive and process the message and execute the executable command or pass along the executable command for execution by one or more other controllers of the pump assembly.

If a main controller of a pump assembly is the sole channel through which an electronic device can communicate particular information between the electronic device and one or more other controllers of the pump assembly, this can be undesirable in certain instances because the main controller can introduce delay, control limits, or errors to the communication between the electronic device and the one or more other controllers. In certain instances, the main controller may devote resources to communicating with the electronic device, which may negatively affect (for example, delay or interrupt) provision of negative pressure wound therapy.

The pump assemblies as described herein can overcome such challenges, in certain embodiments, by enabling communication between the electronic device and the one or more other controllers without relying on the main controller to serve as an intermediary for the communication. The lack of the intermediary moreover can be particularly advantageous, in certain embodiments, when device testing and troubleshooting at least because testing and troubleshooting can be made easier and faster through direct rather than indirect communication.

In some embodiments, a pump assembly can include a communications controller (for instance, a wireless/GPS controller) that may directly communicate with an electronic device without a main controller of the pump assembly functioning as an arbiter between the electronic device and the communications controller. The communications between the electronic device and the communications controller can be via wired communication (for instance, Universal Serial Bus (USB) communication) or wireless communication. The electronic device can send executable commands, such as attention (AT) commands, to the communications controller for execution by the communications controller. One executable command can, for example, cause the communications controller to transition from operating on one network to operating on a different network, such as from a cellular network operated by one provider to a different cellular network operated by a different provider. Moreover, the electronic device can communicate about or change settings of the communications controller without affecting (for example, interrupting) therapy being performed by the pump assembly under control of the main controller.

System Overview

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein; as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. For example, the port can be Renays Soft Port available from Smith & Nephew. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapor permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

The pump assembly 150 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Figure 2A:
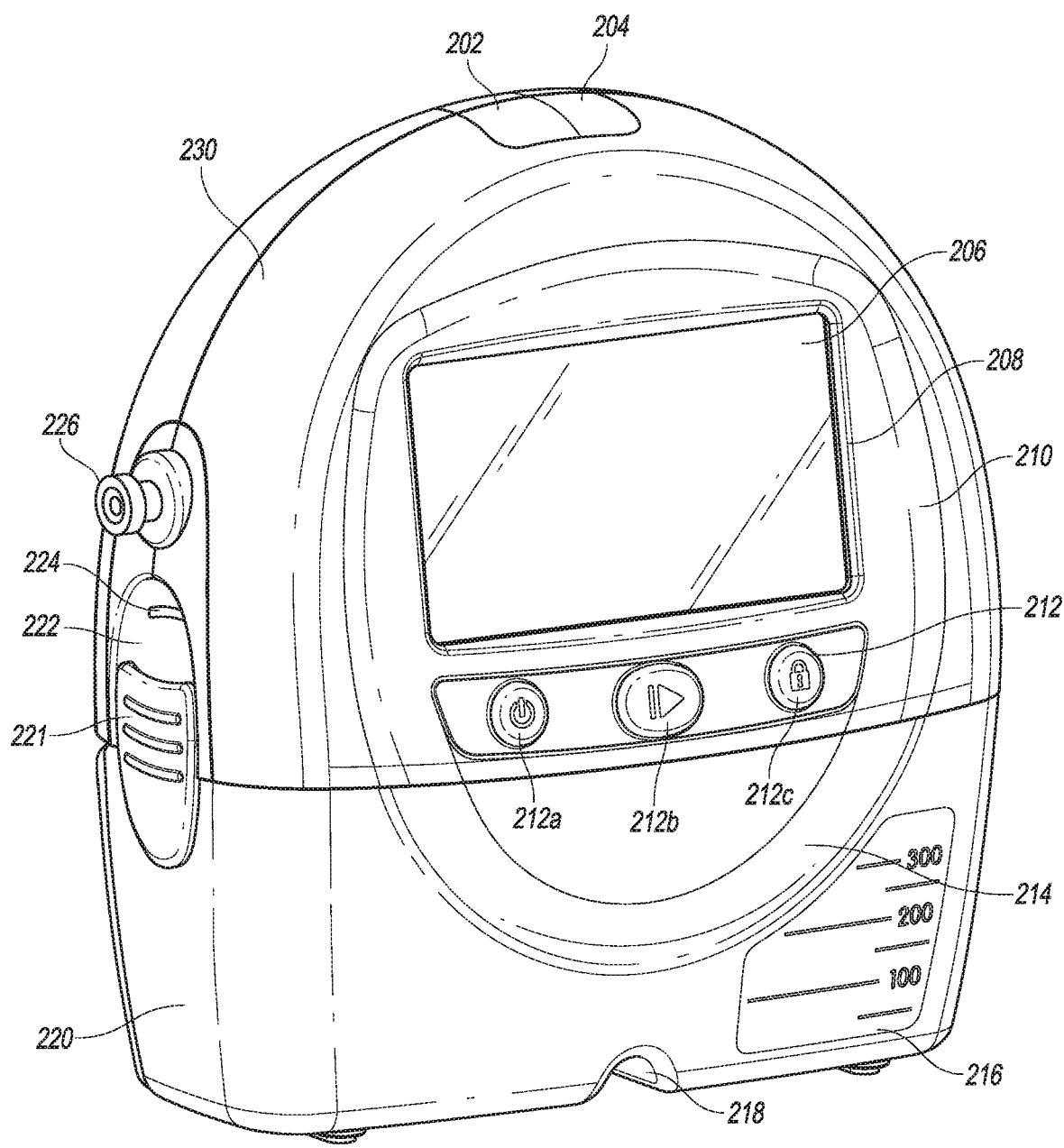
FIGS. 2A, 2B, and 2C illustrate a pump assembly and canister according to some embodiments.

FIG. 2A illustrates a front view of a pump assembly 230 and canister 220 according to some embodiments. As is illustrated, the pump assembly 230 and the canister are connected, thereby forming a negative pressure wound therapy device. The pump assembly 230 can be similar to or the same as the pump assembly 150 in some embodiments.

The pump assembly 230 includes one or more indicators, such as visual indicator 202 configured to indicate alarms and visual indicator 204 configured to indicate status of the TNP system. The indicators 202 and 204 can be configured to alert a user, such as patient or medical care provider, to a variety of operating or failure conditions of the system, including alerting the user to normal or proper operating conditions, pump failure, power supplied to the pump or power failure, detection of a leak within the wound cover or flow pathway, suction blockage, or any other similar or suitable conditions or combinations thereof. The pump assembly 230 can comprise additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 includes a display or screen 206 mounted in a recess 208 formed in a case of the pump assembly. The display 206 can be a touch screen display. The display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 includes one or more keys or buttons 212 configured to allow the user to operate and monitor the operation of the TNP system. As is illustrated, there buttons 212a, 212b, and 212c are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 comprises an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various of these features are omitted or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 comprises two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 canister. The canister 220 comprises a tubing channel 218 for connecting to the conduit 140. In some embodiments, various of these features, such as the gripping portion 214, are omitted or various additional features are added to the canister 220. Any of the disclosed canisters may include or may omit a solidifier.

Figure 2B:
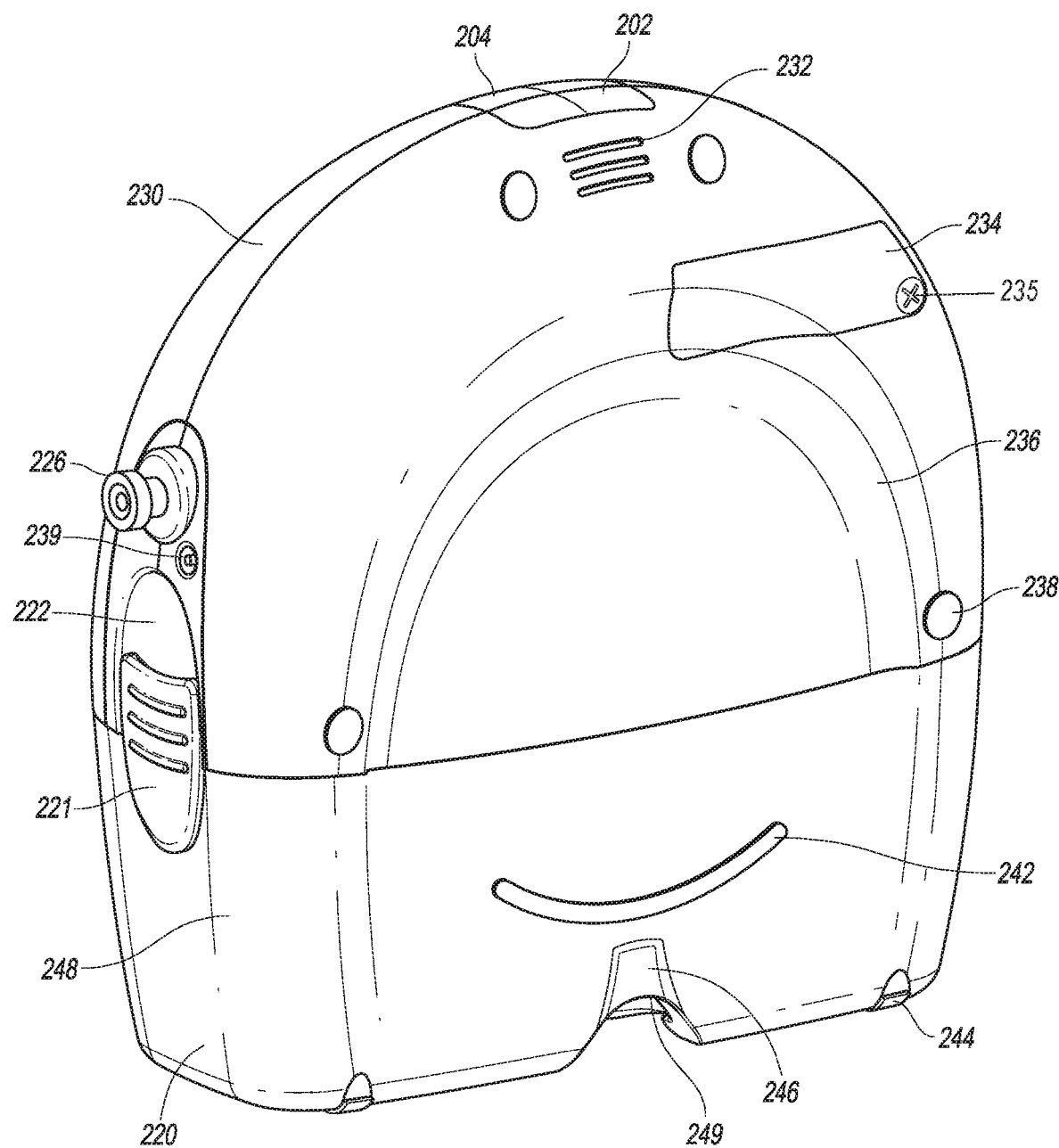

FIG. 2B illustrates a rear view of the pump assembly 230 and canister 220 according to some embodiments. The pump assembly 230 comprises a speaker port 232 for producing sound. The pump assembly 230 includes a filter access door 234 with a screw 235 for removing the access door 234, accessing, and replacing one or more filters, such as antibacterial or odor filters. The pump assembly 230 comprises a gripping portion 236 formed in the case of the pump assembly. The gripping portion 236 can be configured to allow the user to hold the pump assembly 230, such as during removal of the canister 220. The pump assembly 230 includes one or more covers 238 configured to as screw covers or feet or protectors for placing the pump assembly 230 on a surface. The covers 230 can be formed out of rubber, silicone, or any other suitable material. The pump assembly 230 comprises a power jack 239 for charging and recharging an internal battery of the pump assembly. The power jack 239 can be a direct current (DC) jack. In some embodiments, the pump assembly can comprise a disposable power source, such as batteries, so that no power jack is needed.

The canister 220 includes one or more feet 244 for placing the canister on a surface. The feet 244 can be formed out of rubber, silicone, or any other suitable material and can be angled at a suitable angle so that the canister 220 remains stable when placed on the surface. The canister 220 comprises a tube mount relief 246 configured to allow one or more tubes to exit to the front of the device. The canister 220 includes a stand or kickstand 248 for supporting the canister when it is placed on a surface. As explained below, the kickstand 248 can pivot between an opened and closed position. In closed position, the kickstand 248 can be latched to the canister 220. The kickstand 248 can be made out of an opaque material, such as plastic, or a transparent material. The kickstand 248 includes a gripping portion 242 formed in the kickstand. The gripping portion 242 can be configured to allow the user to place the kickstand 248 in the closed position. The kickstand 248 comprises a hole 249 to allow the user to place the kickstand in the open position. The hole 249 can be sized to allow the user to extend the kickstand using a finger.

Figure 2C:
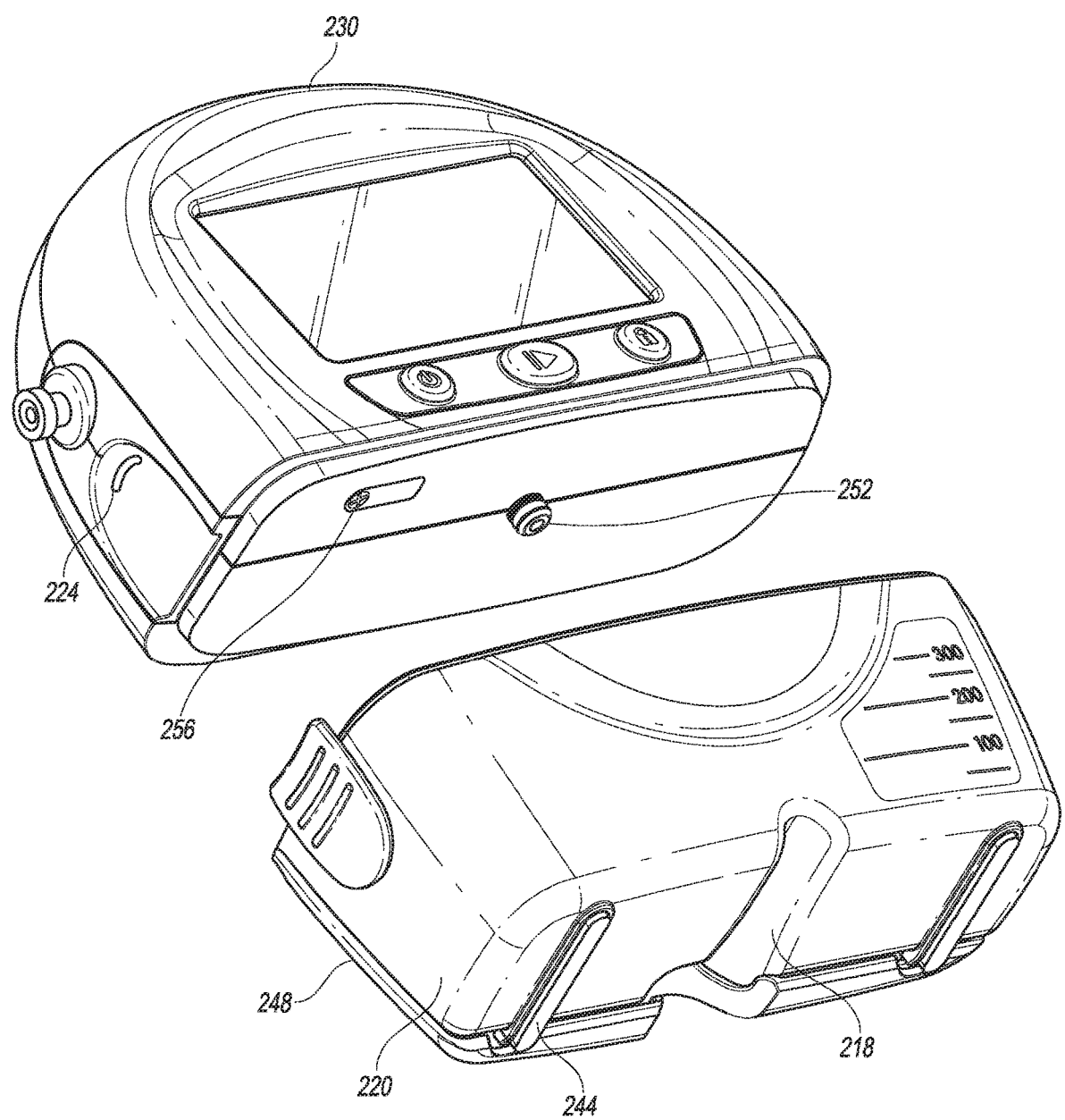

FIG. 2C illustrates a view of the pump assembly 230 separated from the canister 220 according to some embodiments. The pump assembly 230 includes a vacuum attachment, connector, or inlet 252 through which a vacuum pump communicates negative pressure to the canister 220. The pump assembly aspirates fluid, such as gas, from the wound via the inlet 252. The pump assembly 230 may include an access door 256 configured to allow access to one or more serial, parallel, or hybrid data transfer connector interfaces, such as USB, SD, Compact Disc (CD), DVD, FireWire, Thunderbolt, PCI Express, and the like. Additionally or alternatively, one or more serial, parallel, or hybrid data transfer connector interfaces may be accessed through the access door 234. The connector interfaces can be connector ports.

Figure 9A:
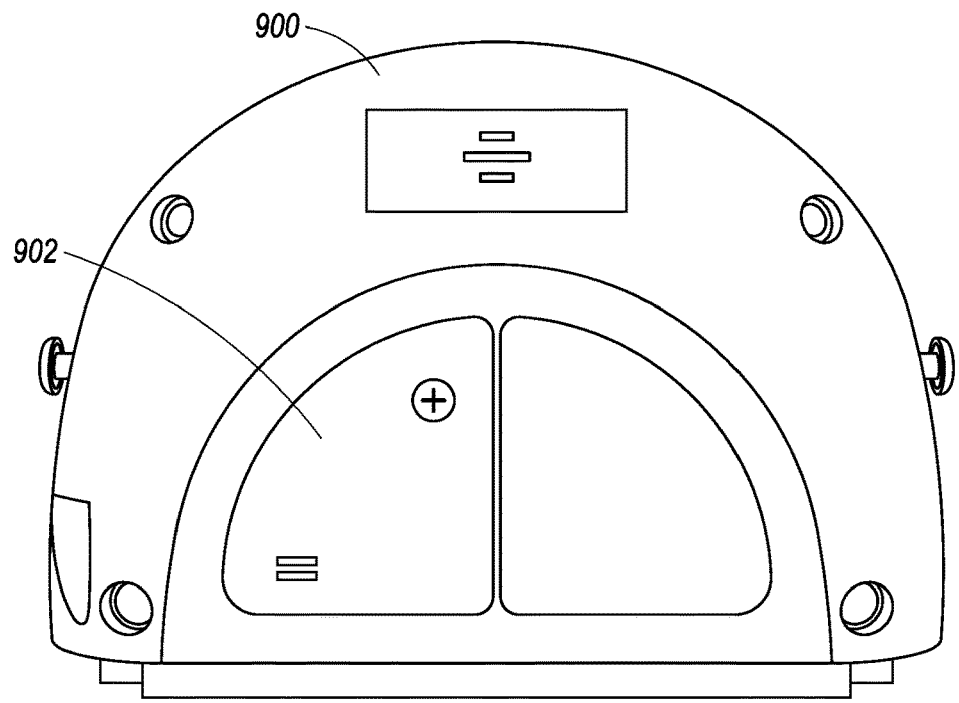
FIGS. 9A and 9B illustrate another pump assembly according to some embodiments.
Figure 9B:
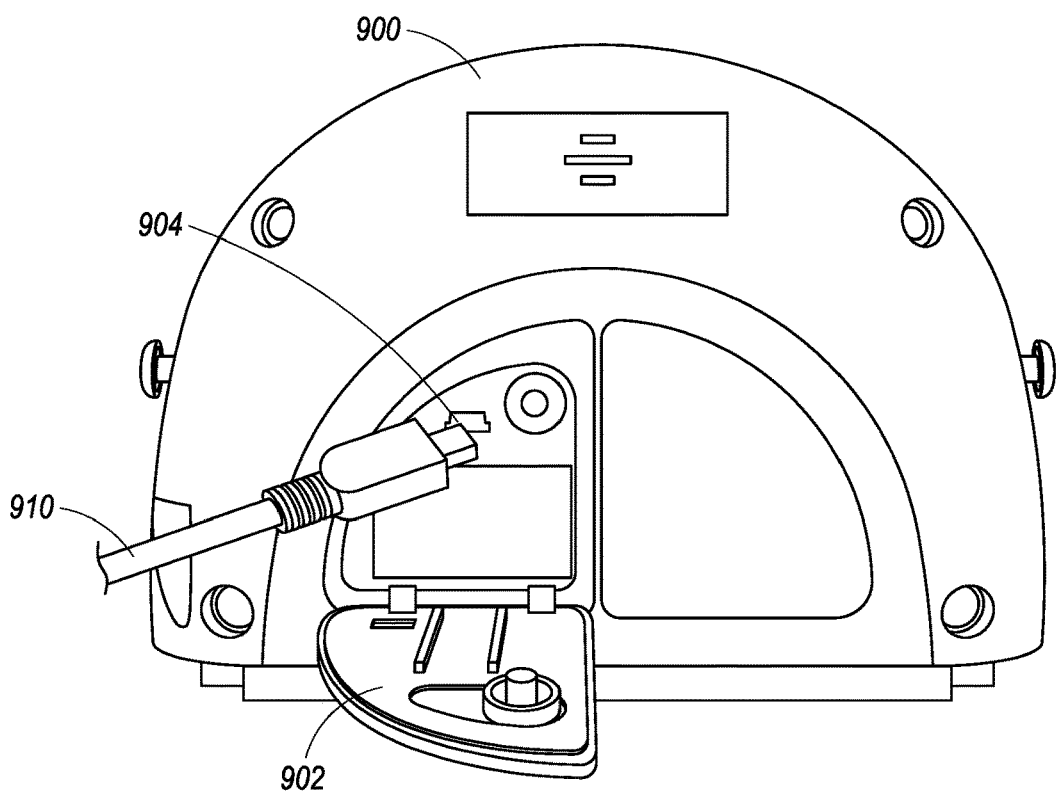
Figure 10:
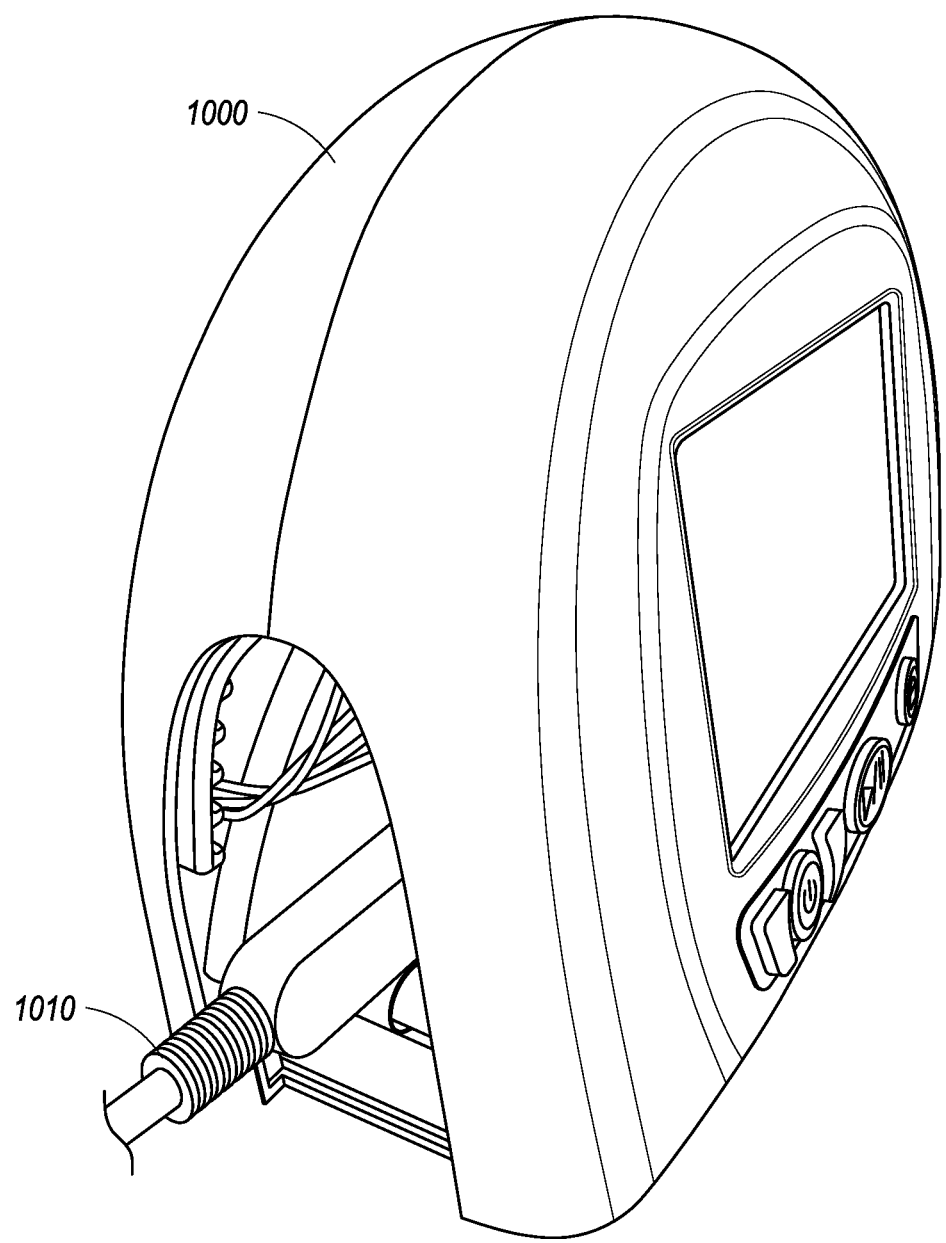
FIG. 10 illustrates yet another pump assembly according to some embodiments.

A pump assembly may include one or more additional or alternative access mechanisms, such as illustrated with respect to FIGS. 9A, 9B, and 10, to access one or more serial, parallel, or hybrid data transfer connector interfaces of the pump assembly. FIGS. 9A and 9B illustrate a view of a pump assembly 900 (similar to the pump assembly 230) that has an access door 902 through which one or more connectors, such as a mini USB connector 910, can access one or more serial, parallel, or hybrid data transfer connector interfaces of the pump assembly 900, including a mini USB connector interface 904, FIG. 10 illustrates a view of a pump assembly 1000 (similar to the pump assembly 230) that includes a side access door which has been removed and through which one or more connectors, such as a mini USB connector 1010, can access one or more serial, parallel, or hybrid data transfer connector interfaces of the pump assembly 1000.

Figure 3A:
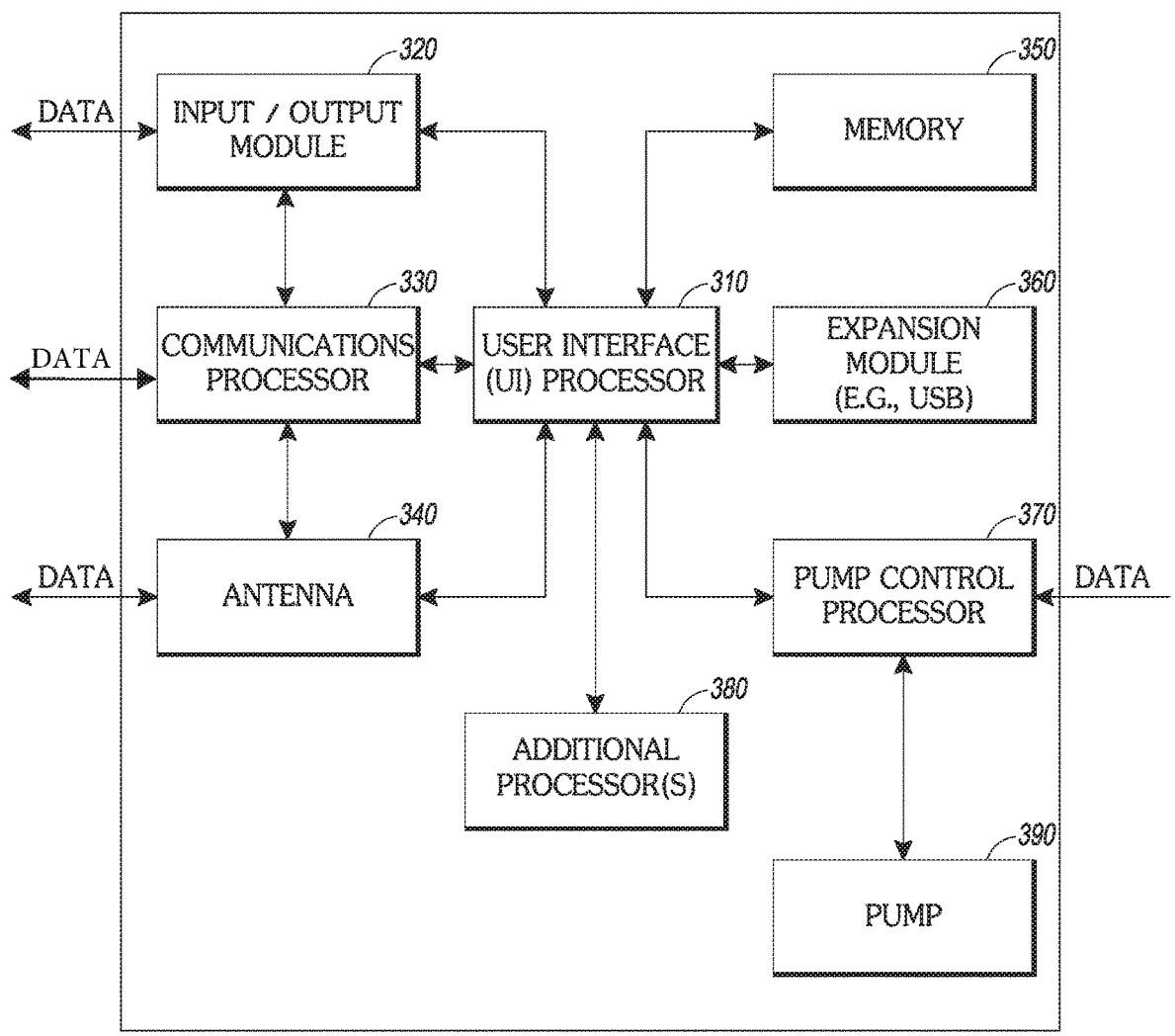
FIG. 3A illustrates an electrical component schematic of a pump assembly according to some embodiments.

FIG. 3A illustrates an electrical component schematic of a pump assembly 300, such as the pump assembly 230, according to some embodiments. Electrical components can operate to accept user input, provide output to the user, operate the pump assembly and the TNP system, provide network connectivity, and so on. Electrical components can be mounted on one or more printed circuit boards (PCBs) that mechanically support and electrically connect electronic components using conductive tracks, pads and other features etched from copper sheets laminated onto a non-conductive substrate. Components, such as capacitors, resistors, or active devices, can be soldered on the PCBs or embedded in the substrate. PCBs can be single sided (one copper layer), double sided (two copper layers) or multi-layer (outer and inner layers), and conductors on different layers can be connected with vias. As is illustrated, the pump assembly can include multiple processors.

The pump assembly can comprise a user interface processor or controller 310 that can function as a main processor and be configured to operate one or more components for accepting user input and providing output to the user, such as the display 206, buttons 212, etc. Input to the pump assembly and output from the pump assembly can controlled by an input/output (I/O) module 320, For example, the I/O module can receive data from one or more ports, such as serial, parallel, hybrid ports, and the like. The processor 310 also receives data from and provides data to one or more expansion modules 360, such as one or more USB ports, SD ports, CD drives, DVD drives, FireWire ports, Thunderbolt ports, PCI Express ports, and the like. The processor 310, along with other controllers or processors, stores data in one or more memory modules 350, which can be internal or external to the processor 310. Any suitable type of memory can be used, including volatile or non-volatile memory, such as RAM, ROM, magnetic memory, solid-state memory, magnetoresistive random-access memory (MRAM), and the like.

In some embodiments, the processor 310 can be a general purpose controller, such as a low-power processor. In other embodiments, the processor 310 can be an application specific processor. The processor 310 can be configured as a "central" processor in the electronic architecture of the pump assembly, and the processor 310 can coordinate the activity of other processors, such as a pump control processor 370, communications processor 330, and one or more additional processors 380 (e.g., processor for controlling the display 206, processor for controlling the buttons 212, etc.). The processor 310 can run a suitable operating system, such as a Linux, Windows CE, VxWorks, etc.

The pump control processor 370 can be configured to control the operation of a negative pressure pump 390. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The pump control processor 370 can measure pressure in a fluid flow path, using data received from one or more pressure sensors, calculate the rate of fluid flow, and control the pump. The pump control processor 370 can control a pump motor so that a desired level of negative pressure is achieved in the wound cavity 110. The desired level of negative pressure can be pressure set or selected by the user. In various embodiments, the pump control processor 370 controls the pump (e.g., pump motor) using pulse-width modulation (PWM). A control signal for driving the pump can be a 0-100% duty cycle PWM signal. The pump control processor 370 can perform flow rate calculations and detect various conditions in a flow path. The pump control processor 370 can communicate information to the processor 310. The pump control processor 370 can include internal memory or can utilize memory 350. The pump control processor 370 can be a low-power processor.

A communications processor 330 can be configured to provide wired or wireless connectivity. The communications processor 330 can utilize one or more antennas 340 for sending and receiving data. The communications processor 330 can provide one or more of the following types of connections: Global Positioning System (GPS) technology, cellular connectivity (e.g., 2G, 3G, LTE, 4G, 5G, SIM chip), WiFi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software or firmware, and the like. The communications processor 330 can provide dual GPS/cellular functionality. Cellular functionality can, for example, be 3G functionality. The pump assembly can include a subscriber identity module (SIM) card, and SIM-based positional information can be obtained.

The communications processor 330 can also be electrically coupled to one or more serial, parallel, or hybrid data transfer connector interfaces or another type of interface through which the communications processor 330 can directly receive data or commands without receiving the data or commands through or from the processor 310. For instance, the data transfer connector interfaces can include one or more USB ports, SD ports, CD drives, DVD drives, FireWire ports, Thunderbolt ports, PCI Express ports, and the like. The data transfer connector interfaces can, for instance, be part of the communications processor 330 or part of the input/output (I/O) module 320.

The communications processor 330 can communicate information to the processor 310 and receive information from the processor 310. The communications processor 330 can include internal memory or can utilize memory 350. The communications processor 330 can be a low-power processor.

Using the connectivity provided by the communications processor 330, the device can upload any of the data stored, maintained, or tracked by the pump assembly. The device can also download various operational data, such as therapy selection and parameters, firmware and software patches and upgrades, and the like.

Figure 3B:
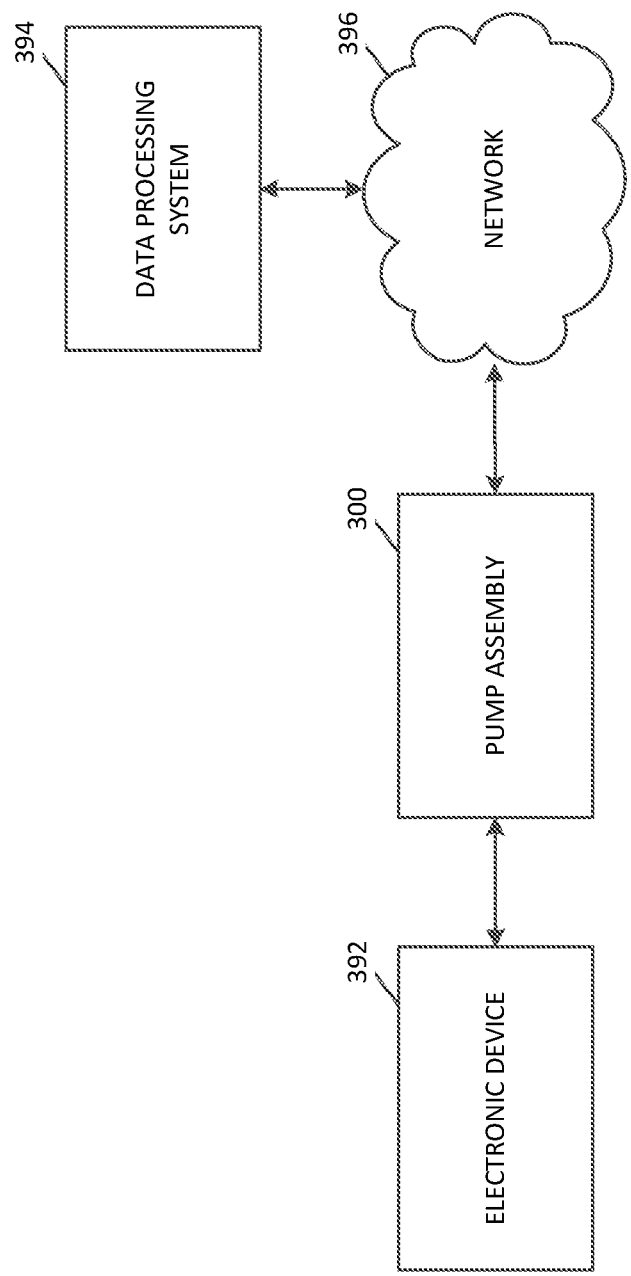
FIG. 3B illustrates communication with the pump assembly of FIG. 3A according to some embodiments.

FIG. 3B illustrates example communication between the pump assembly 300 and multiple other devices, including an electronic device 392 (such as a laptop, tablet, smart phone, or another computing device) and a data processing system 394. The electronic device 392 and the data processing system 394 can exchange data or commands (for instance, commands of a Hayes command set) with the pump assembly 300 via one or more of the input/output (I/O) module 320, a serial, parallel, or hybrid data transfer connector interface of the communications processor 330, and the antenna 340. The electronic device 392 can, for example, interrogate or reprogram the communications processor 330. The electronic device 392 may not be supported by a housing of the pump assembly 300. The data processing system 394 may communicate with the pump assembly 300 via a network 396. The network 396 can be a communication network, such as a wired communication network or a wireless communication network like a cellular communication network.

The communications processor 330 can receive and execute an executable command from the electronic device 392 without interrupting wound therapy being performed by the pump assembly 300 and without the processor 310 being operational (for instance, powered). Moreover, the communications processor 330 can receive and execute an executable command from the electronic device 392 that instructs and causes the communications processor 330 to: test an operation of the communications processor 330, transmit the hardware or software version data for the communications processor 330 to the electronic device 392, change a setting associated with operation of the communications processor 330, communicate data via one communication network rather than another communication network, perform an operation associated with a communication network over which the communications processor 330 transmits data, or the like. The communications processor 330 can enter a data mode in which data processed by the communications processor 330 is not executed and a command mode in which data processed by the communications processor 330 is executed. In some implementations, the communication processor 330 can execute certain executable commands (such as those described herein) directly without communicating such commands to or otherwise involving the processor 310. The communication processor 330 can communicate to or otherwise involve the processor 310 for execution of certain other executable commands, such as executable commands that relate to provision of therapy.

In one implementation, the electronic device 392 can be a personal computer (PC) that communicates with the pump assembly 300. The electronic device 392 can be first connected to the pump assembly 300 and the pump assembly 300—or at least the communications processor 330—can be unpowered. The pump assembly 300—or at least the communications processor 330—can then be powered and a wait period of 30 seconds can be initiated and completed. On the electronic device 392, a terminal program (for instance, PuTTY HyperTerminal) can next be opened and connected to a communications port through which the electronic device 392 is connected to the pump assembly 300. The terminal program can subsequently be used to provide executable commands to the communications processor 330, and the terminal program can display any responses from the communications processor 330.

Figure 4A:
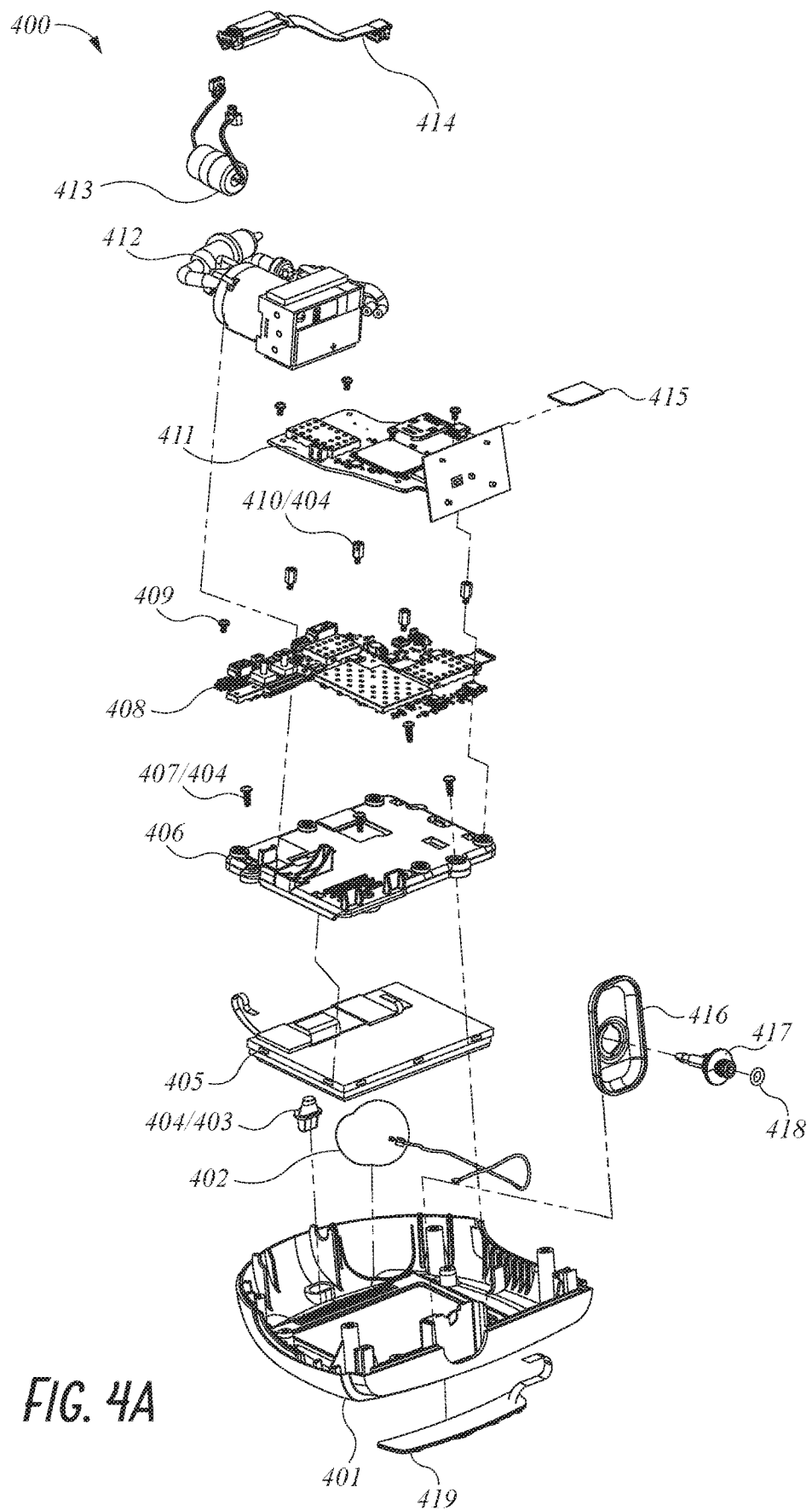
FIGS. 4A, 4B, 4C, 4D, 4E, and 4F illustrate a pump assembly according to some embodiments.
Figure 4B:
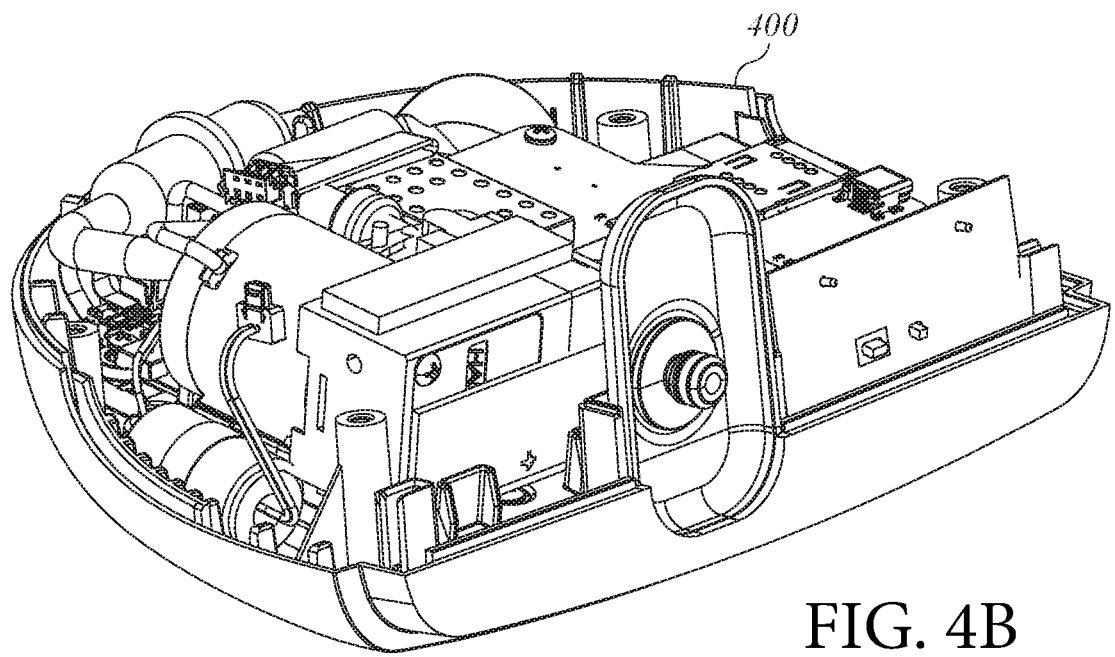
Figure 4C:
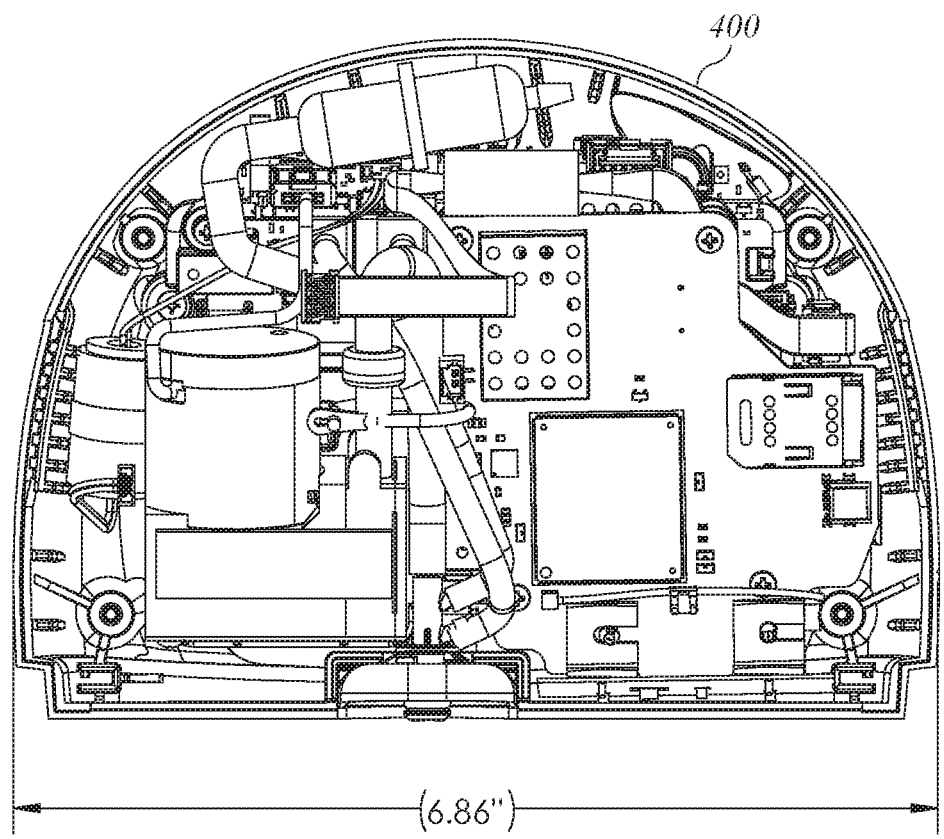
Figure 4D:
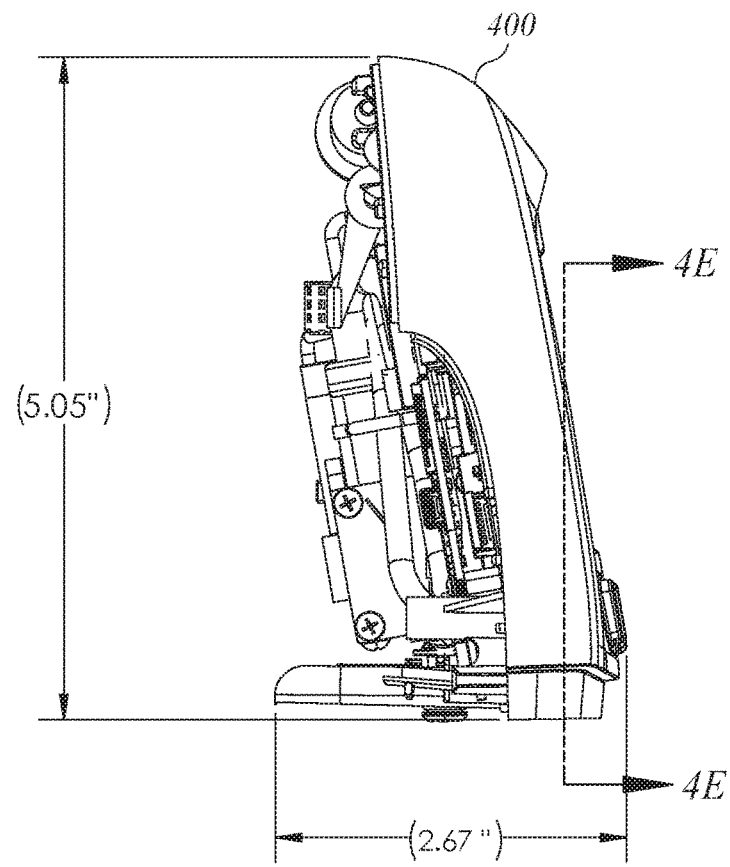
Figure 4E:
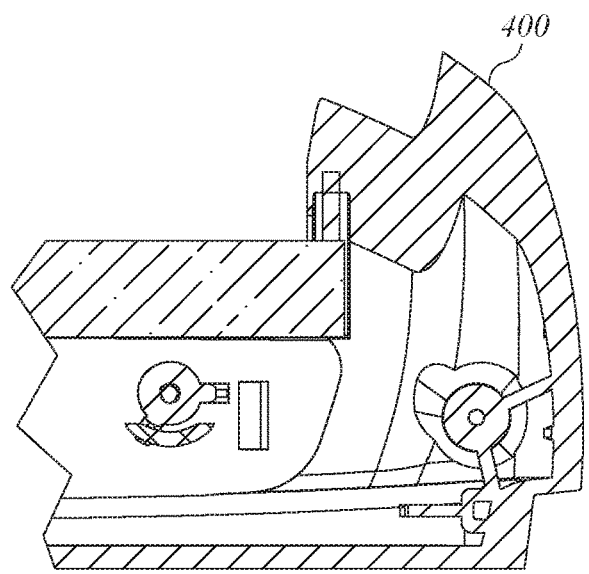
Figure 4F:
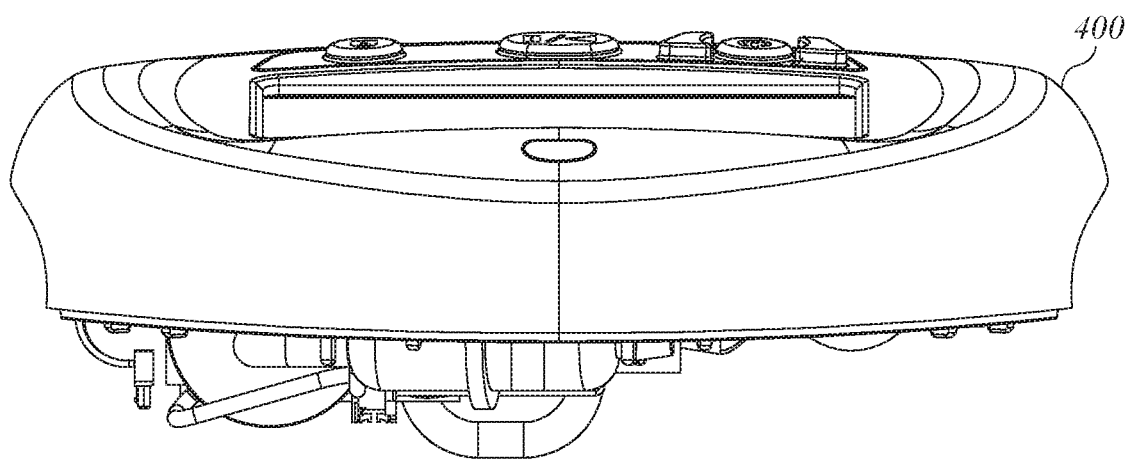

FIG. 4A illustrates exploded view of a pump assembly 400, such as the pump assembly 230, according to some embodiments. The illustrated view can correspond to the front portion of the pump assembly 400. The components of the pump assembly 400 can include: a front enclosure 401, a GPS antenna 402, a status light pipe 403, adhesives 404, a liquid crystal display (LCD) 405, a chassis and LCD circuit board assembly 406, screws 407, a main circuit board assembly 408 (on which the processor 310 and the pump control processor 370 can be mounted in some implementations), screws 409, standoffs 410, a communications circuit board assembly 411 (on which the communications processor 330 can be mounted in some implementations), a negative pressure source 412, a power entry cable 413, a USB cable assembly 414, a subscriber identity module (SIM) card 415, a bottom enclosure 416, a canister connector 417, a canister connector O-ring 418, and a keypad 419. FIGS. 4B-4F illustrate multiple views of the pump assembly 400 according to some embodiments. The dimensions included in FIGS. 4B-4F are provided in inches.

Although FIGS. 4A-4F show particular components included as part of the pump assembly 400, some components may be removed or other components may be added in other implementations.

Figure 5A:
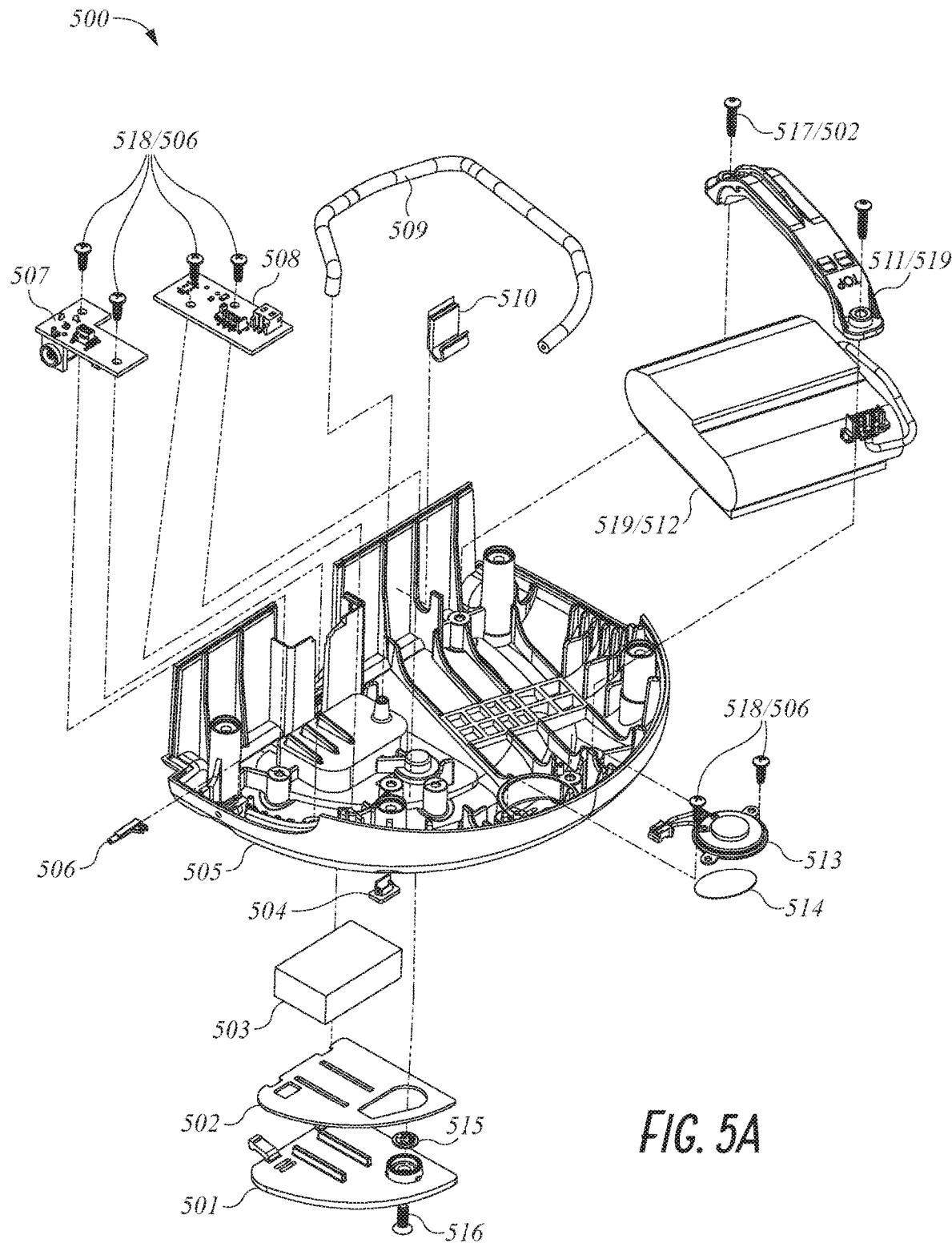
FIGS. 5A, 5B, 5C, 5D, and 5E illustrate a pump assembly according to some embodiments.
Figure 5B:
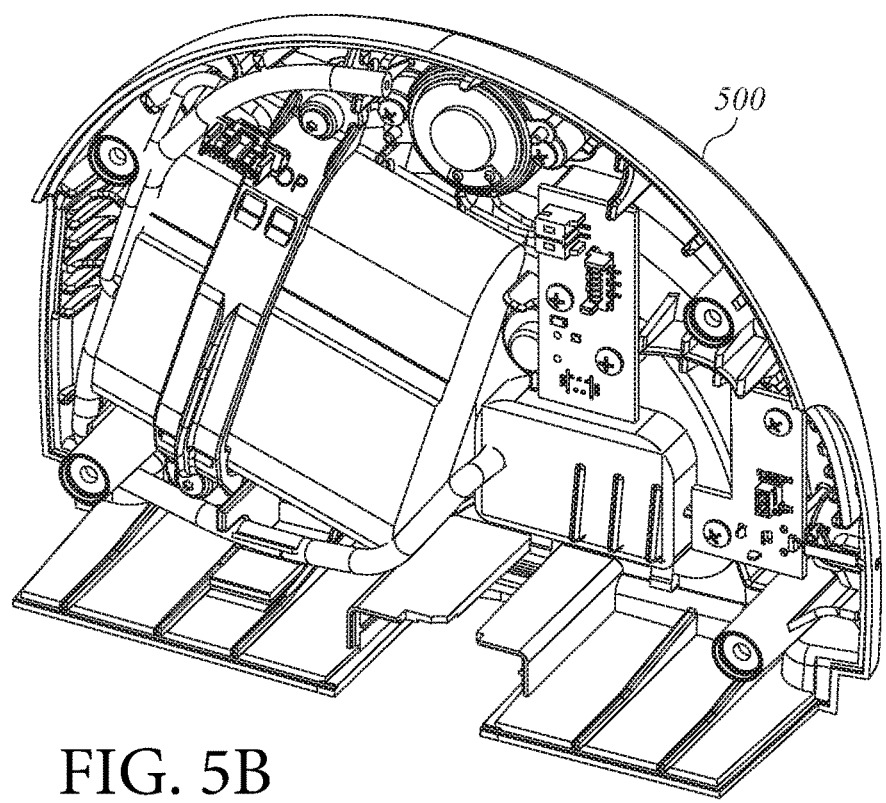
Figure 5C:
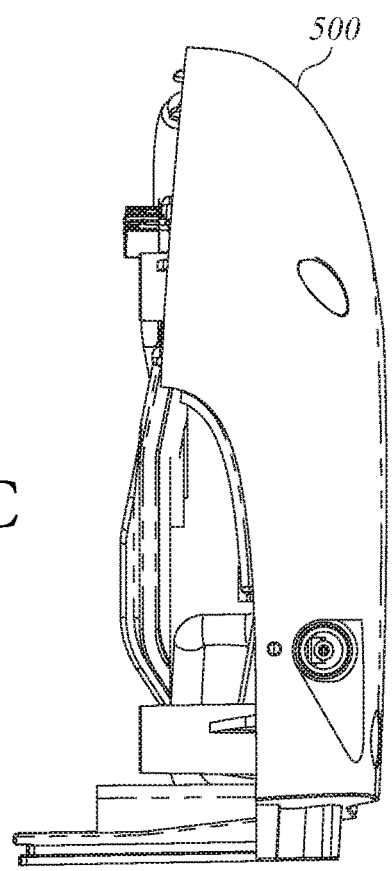
Figure 5D:
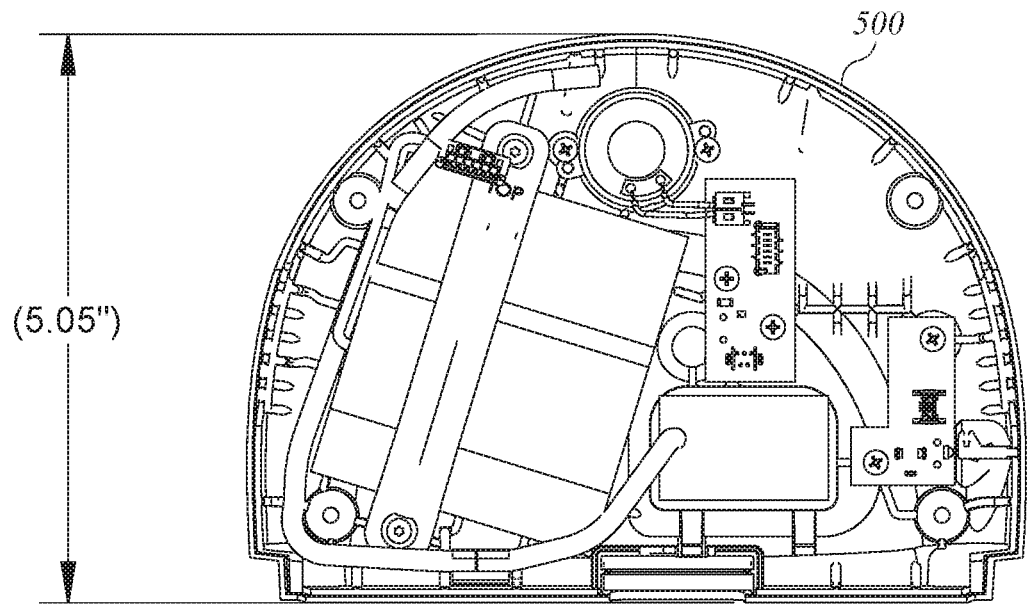
Figure 5E:
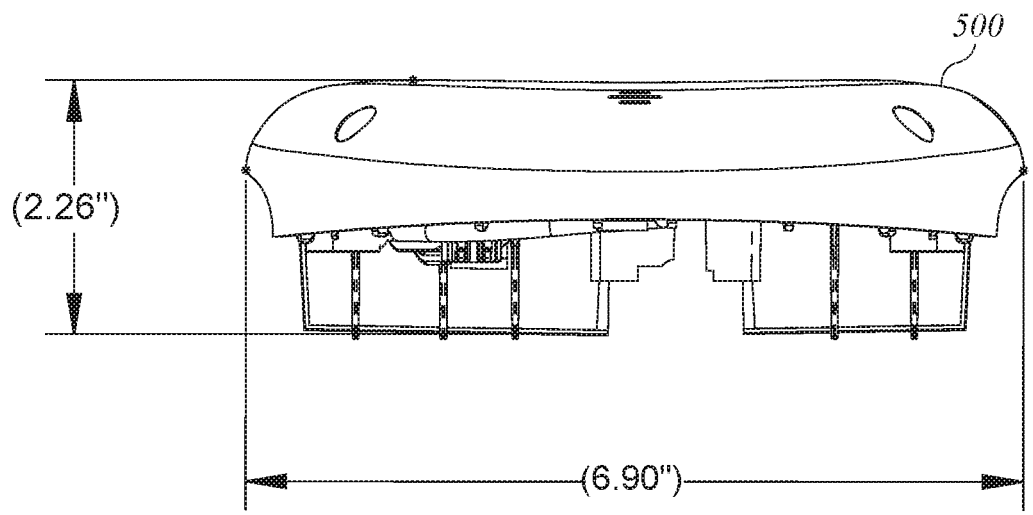

FIG. 5A illustrates exploded view of a pump assembly 500, such as the pump assembly 230, according to some embodiments. The illustrated view can correspond to the back portion of the pump assembly 500. The illustrated components of the pump assembly 500 can be configured to couple to the components of the pump assembly 400 to form an integral pump assembly. The components of the pump assembly 500 can include: an access door 501 (which can be the same as access door 234), a filter enclosure gasket 502, a filter 503 (for example, antibacterial filter, odor filter, and the like), a mini USB port cover 504, a back enclosure 505, a power entry light pipe 506, a power entry circuit board assembly 507, a USB circuit board assembly 508 (on which the I/O module 320 can be mounted in some implementations), a tubing outlet 509, a clip 510, a battery bracket 511, a battery 512, a speaker assembly 513, a speaker filter 514, a push nut 515, a screw 516 (which can be the same as the screw 235), screws 517, screws 518, and foam tape 519. FIGS. 5B-5E illustrate multiple views of the pump assembly 500 according to some embodiments. The dimensions included in FIGS. 5B-5E are provided in inches.

Although FIGS. 5A-5F show particular components included as part of the pump assembly 500, some components may be removed or other components may be added in other implementations.

Device Electronics and Communication

Figure 6A:
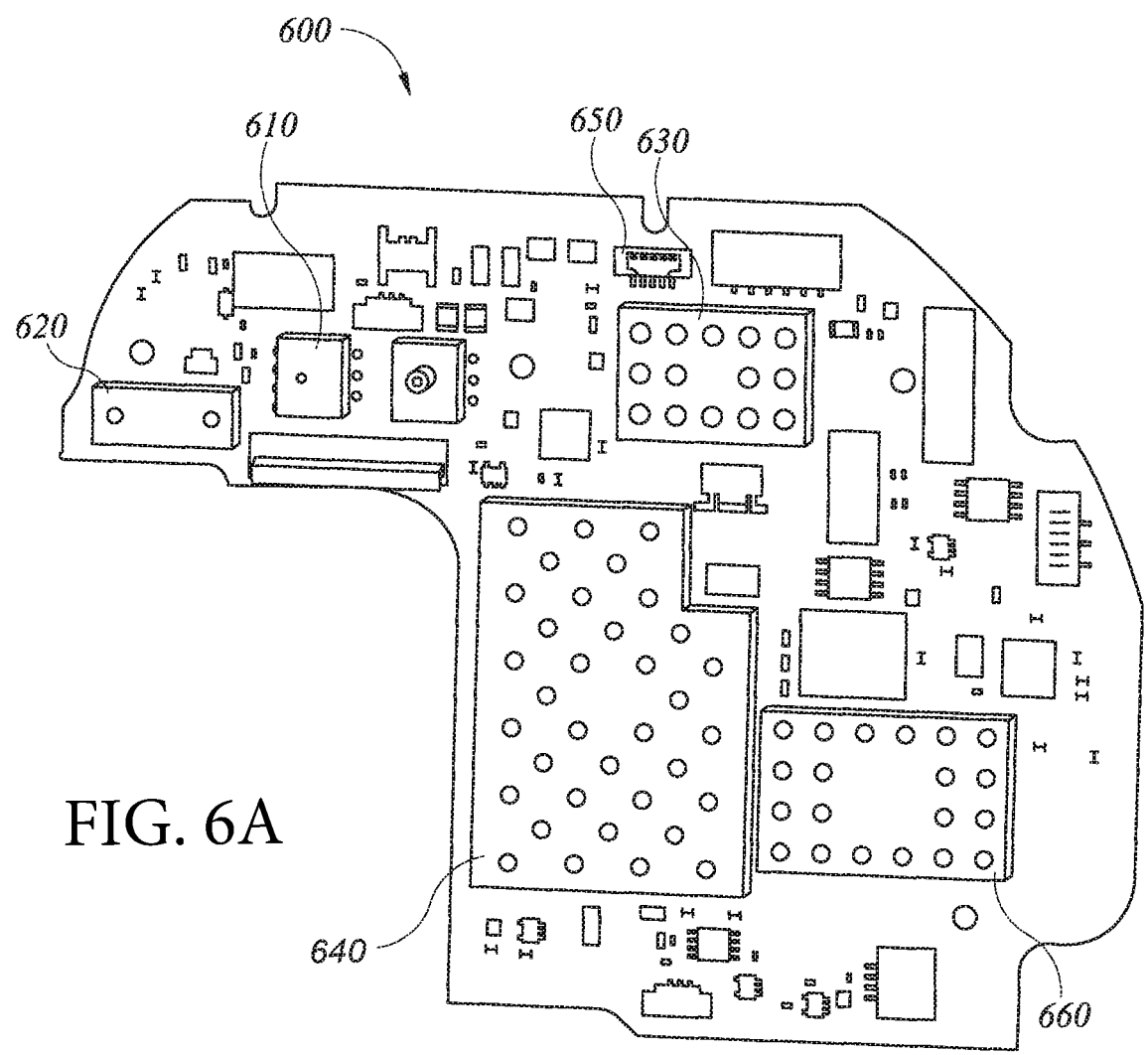
FIGS. 6A and 6B illustrate a front and back of a main circuit board assembly according to some embodiments.
Figure 6B:

FIG. 6A illustrates a front of a main PCB assembly 600 of a pump assembly, such as the pump assembly 230, according to some embodiments. The main PCB assembly 600 can, for example, be an embodiment of the main circuit board assembly 408. The main PCB assembly 600 can include a digital signal processor 610 for controlling a source of negative pressure, an electromagnetic compatibility shield 620 for an LED backlight (for example, to protect against high voltages like 12 V rather than 3 V), a shielded battery charger 630, a shielded main microcontroller 640 (which can be similar to or the same as the processor 310), a battery connector 650, and a shielded regulator 660 for digital circuitry. FIG. 6B illustrates a back of the main PCB assembly 600.

Figure 7A:
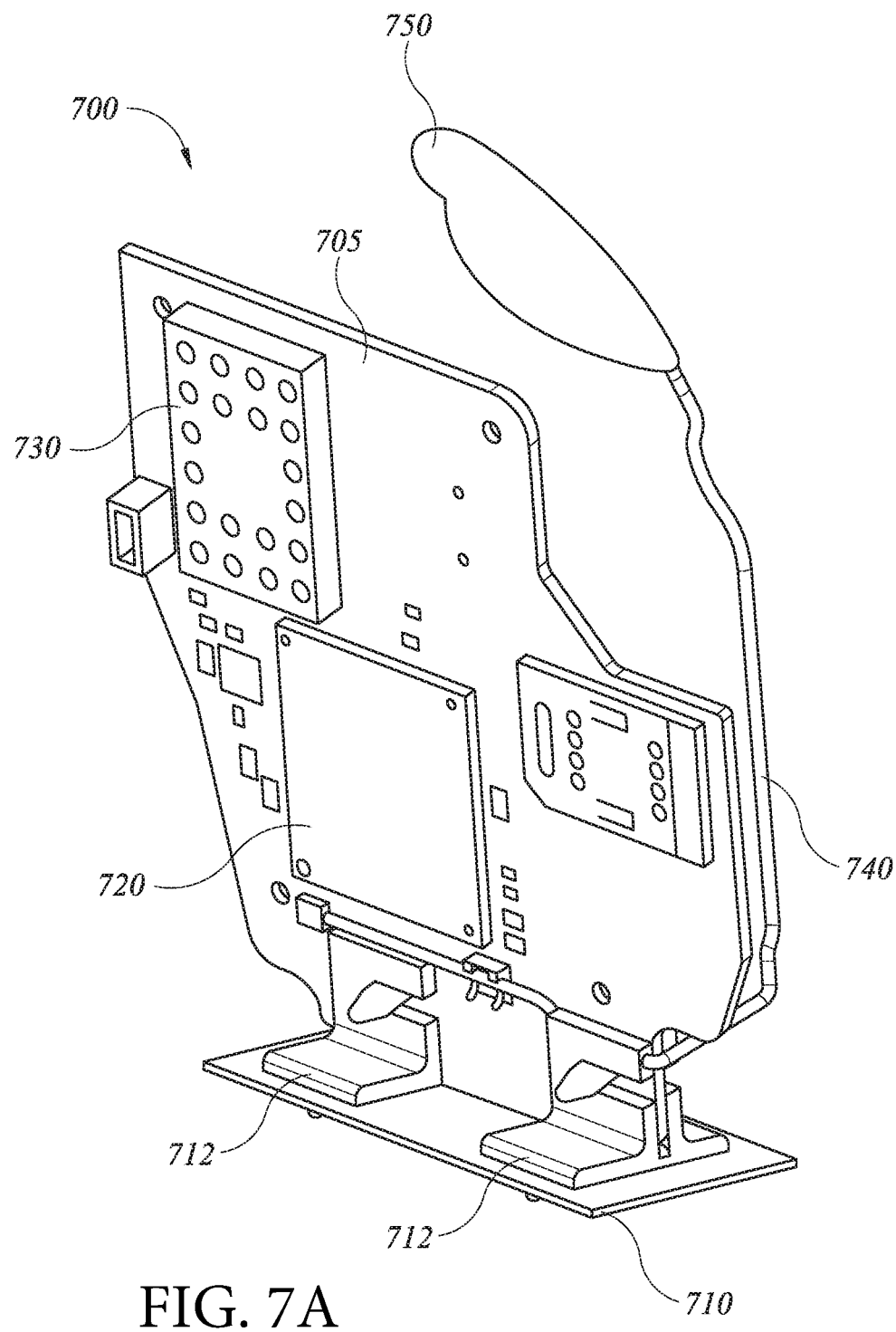
FIGS. 7A and 7B illustrate a communications circuit board assembly according to some embodiments.
Figure 7B:
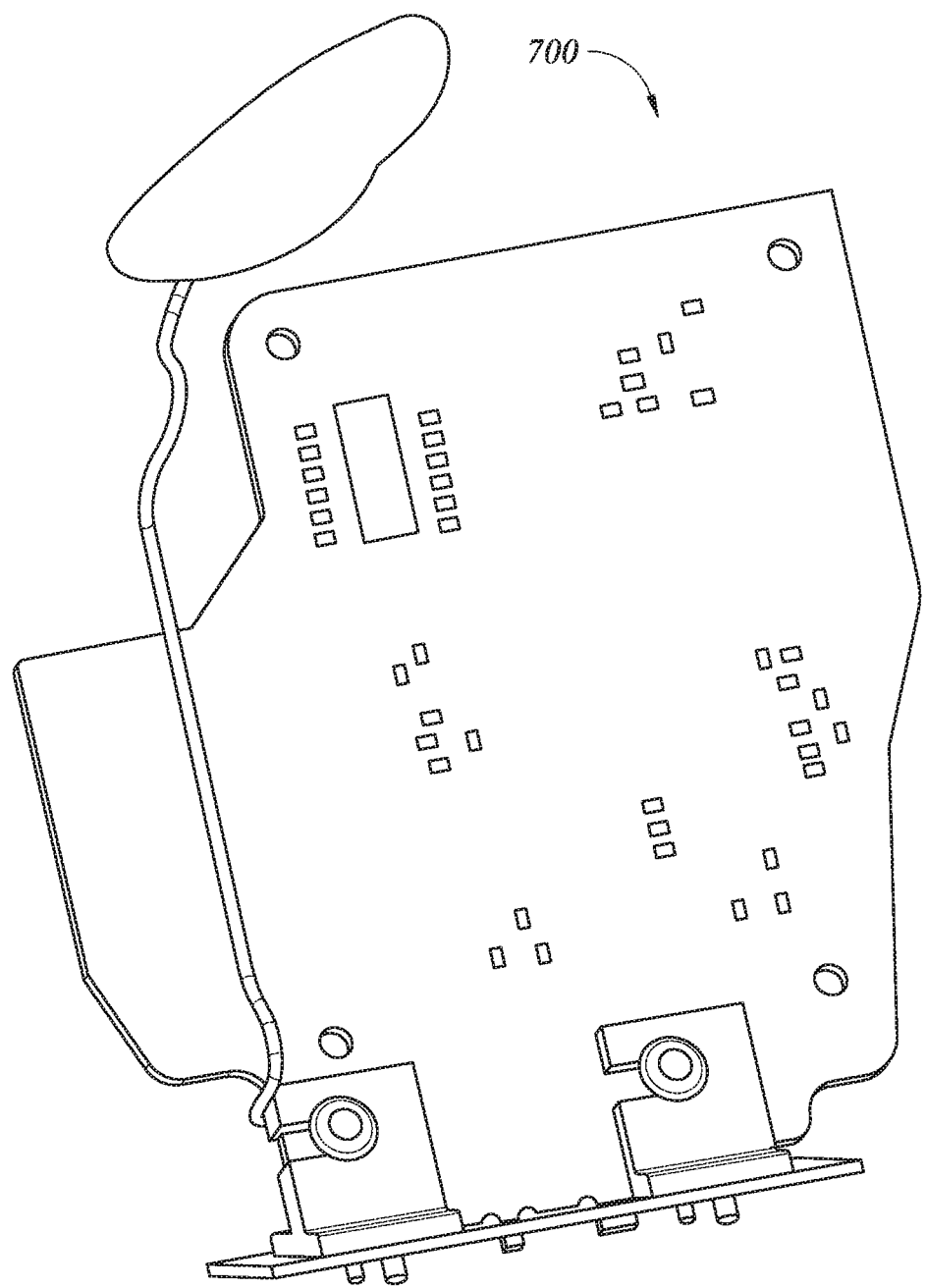

FIGS. 7A and 7B illustrate a front and back of a wireless communication PCB assembly 700 of a pump assembly, such as the pump assembly 230, according to some embodiments. The wireless communication PCB assembly 700 can, for example, be an embodiment of the communications circuit board assembly 411. The wireless communication PCB assembly 700 can include an antenna board 710 and a PCB 705 with a shielded modem 720 including a wireless communications controller (which can be similar to or the same as the communications processor 330), and a shielded voltage regulator 730. The antenna board 710 can be wireless mobile communications antenna, such a single-, dual-, tri-, quad-, or the like band antenna for communicating via 2G, 3G, LTE, 4G, or the like and be mounted to the communications PCB 705 with mounting brackets 712. The wireless communication PCB assembly 700 can be electrically coupled via a path 740 to a GPS antenna 750, which can be an embodiment of the GPS antenna 402. In addition, the wireless communications controller can electrically couple to a communications interface that enables communication with the wireless communications controller without communicating through the main PCB assembly 600, such as the shielded main microcontroller 640.

Figure 8A:
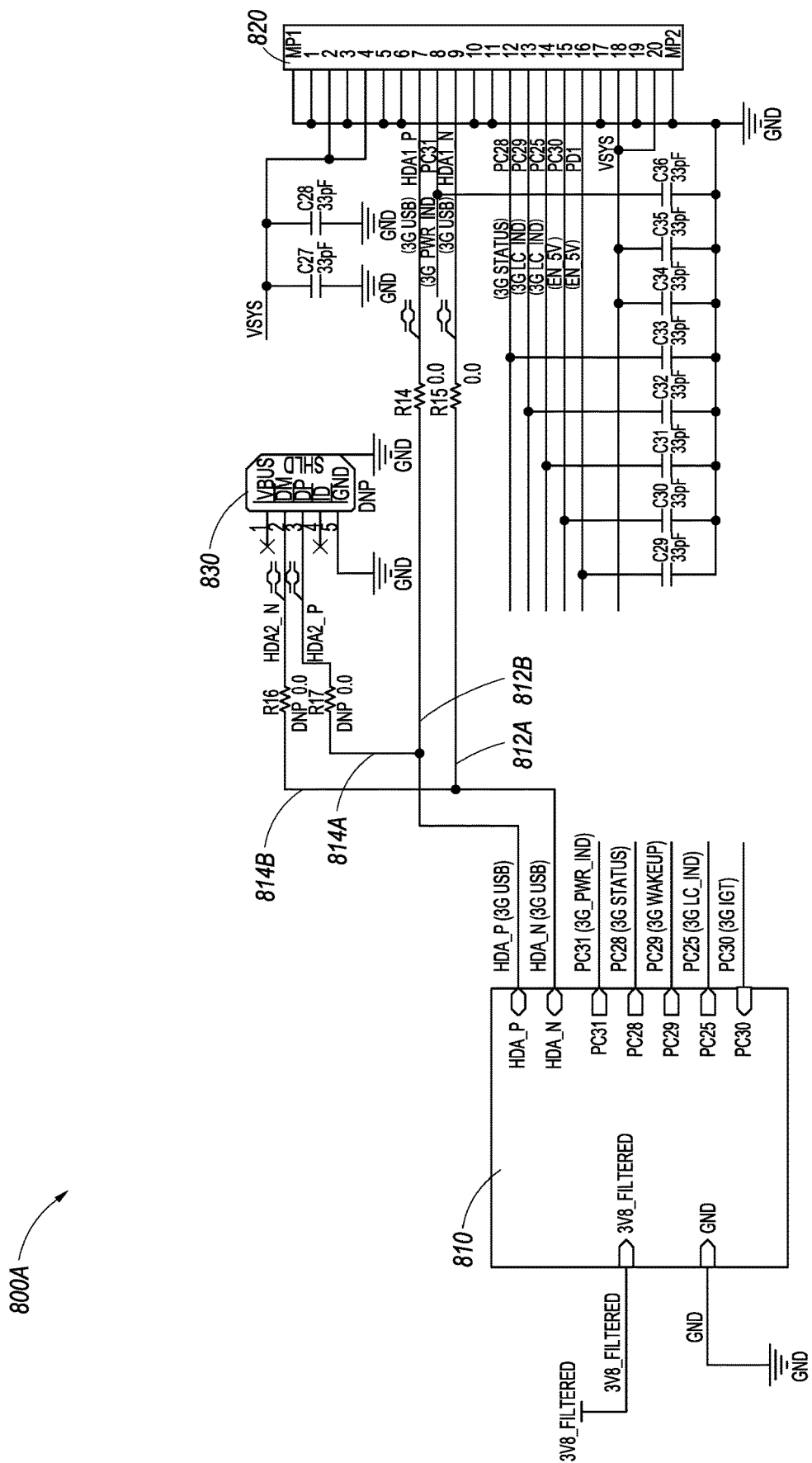
FIGS. 8A and 8B illustrate communications interfaces of a pump assembly according to some embodiments.

FIG. 8A illustrates multiple communications interfaces of various components 800A of a pump assembly, such as the pump assembly 230. The various components 800A can include a wireless communications controller 810, a main microcontroller 820, and a connector port 830. The wireless communications controller 810 can be an implementation of the wireless communications controller of the shielded modem 720, and the main microcontroller 820 can be an implementation of the shielded main microcontroller 640. The connector port 830 can be connected to an electronic device, such as the electronic device 392, to facilitate direct communication between the electronic device and the wireless communications controller 810.

The wireless communications controller 810 can communicate with the main microcontroller 820 via a first path 812A electrically connecting contacts HDA_P and HDA1_P and a second path 812B electrically connecting contacts HDA_N to HDA1_N. The wireless communications controller 810 can communicate with the connector port 830 via a third path 814A electrically connecting contacts HDA_P and HDA2_P and a fourth path 814B electrically connecting contacts HDA_N to HDA2_N. In operation, one of the first and second paths 812A, 812B or the third and fourth paths 814A, 814B may be connected at a time so that either the main microcontroller 820 or the connector port 830 may communicate with the wireless communications controller 810, For example, resistors R16, R17 can be activated or conducting and resistors R14, R15 may not be activated or conducting when the wireless communications controller 810 communicates with the connector port 830, and the resistors R14, R15 can be activated or conducting and the resistors R16, R17 may not be activated or conducting when the wireless communications controller 810 communicates with the main microcontroller 820. In some implementations, resistors R14, R15, R16, and R17 can be replaced with two or more dip switches, relays, or the like to permit connection of the wireless communications controller 810 to the main microcontroller 820 or the connector port 830.

Figure 8B:
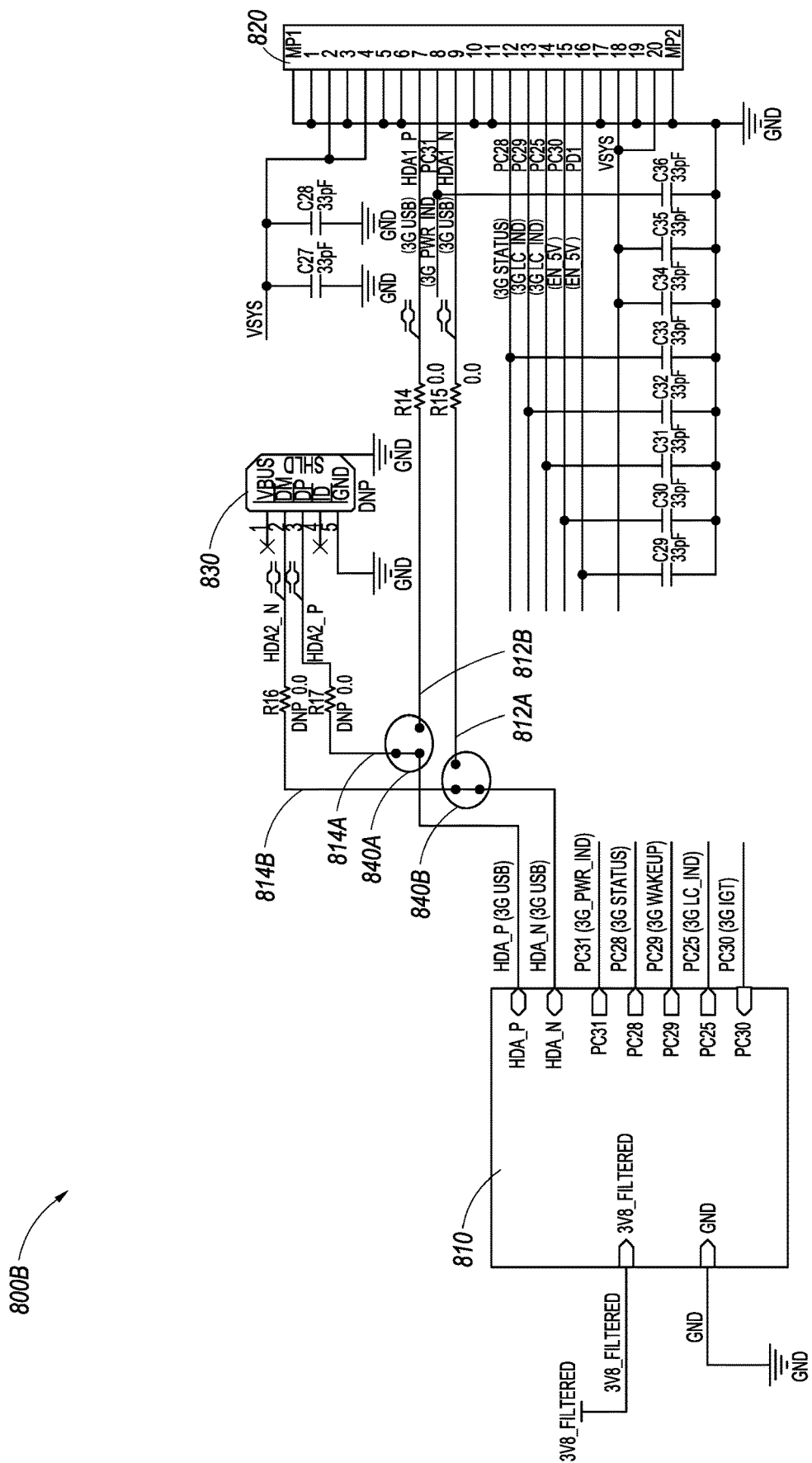

FIG. 8B illustrates multiple communications interfaces of various components 800B of a pump assembly, such as the pump assembly 230. The various components 800B can be similar to the various components 800A with the exception that a first switch 840A and a second switch 840B be used to control the electrical connection of the wireless communications controller 810 to either the main microcontroller 820 or the connector port 830. The first and second switches 840A, 840B can accordingly be considered to adjust a mode of operation of the pump assembly (such as between a normal mode where therapy may be performed and data can be transmitted and received by the main microcontroller 820 via the wireless communications controller 810 and a test mode where cellular or wireless coexistence testing is performed like to send AT commands.

The first and second switches 840A, 840B can, for instance, be part of one or more dual in-line package (DIP) switches. In certain embodiments, the implementation of the various components 800A can be preferred over the implementation of the various components 800B because the first and second switches 840A, 840B may introduce noise or other negative signal artifacts that impede communication with the wireless communications controller 810.

The first and second switches 840A, 840B can, in some implementations, be smart switches, such as analog relay switches, that may be commanded via software. In one example, a display of a pump assembly, such as the display 206, can present a user input that is selected to control a state of one or both of the first and second switches 840A, 840B. In another example, a state of one or both of the first and second switches 840A, 840B can be adjusted via remote communication between a pump assembly and another electronic device. The first and second switches 840A, 840B can be controlled as a serial communication router (for instance, USB, SPI, I2C, or the like), multiplexers, or analog switches. The first and second switches 840A, 840B can be one-time or multi-use fuses in some implementations, which can be desirable in some cases for preprograming code or settings in the wireless communications controller 810 and securing later.

The first and second switches 840A, 840B can be designed so that the pump assembly with the first and second switches 840A, 840B may pass wireless coexistence adjacent channel selectivity testing (for instance, 3G wireless coexistence adjacent channel selectivity testing). The first and second switches 840A, 840B can access the wireless communications controller 810 via another electronic device or a special tool and may be used to analyze or troubleshoot a break in device security. The another electronic device or special tool can moreover send an AT command that allows the another electronic device or special tool to test a carrier for the pump assembly (for example, a cellular network on which the pump assembly communicates using the wireless communications controller 810). In the event of a software or hardware failure or a safety failure, such as to the main microcontroller 820 or another controller of the pump assembly other than the wireless communications controller 810, the first and second switches 840A, 840B can help with analyzing the communication channel between the wireless communications controller 810 and the main microcontroller 820. In some implementations, a SIM card can be connected to the wireless communications controller 810.

Although FIGS. 8A and 8B may describe communication with the wireless communications controller 810, another controller of the pump assembly may be positioned and connected in place of the wireless communications controller 810 enabling the another controller, which may provide alternative or additional functionality relative to the wireless communications controller 810, to communicate with the main microcontroller 820 and the connector port 830.

Figure 11:
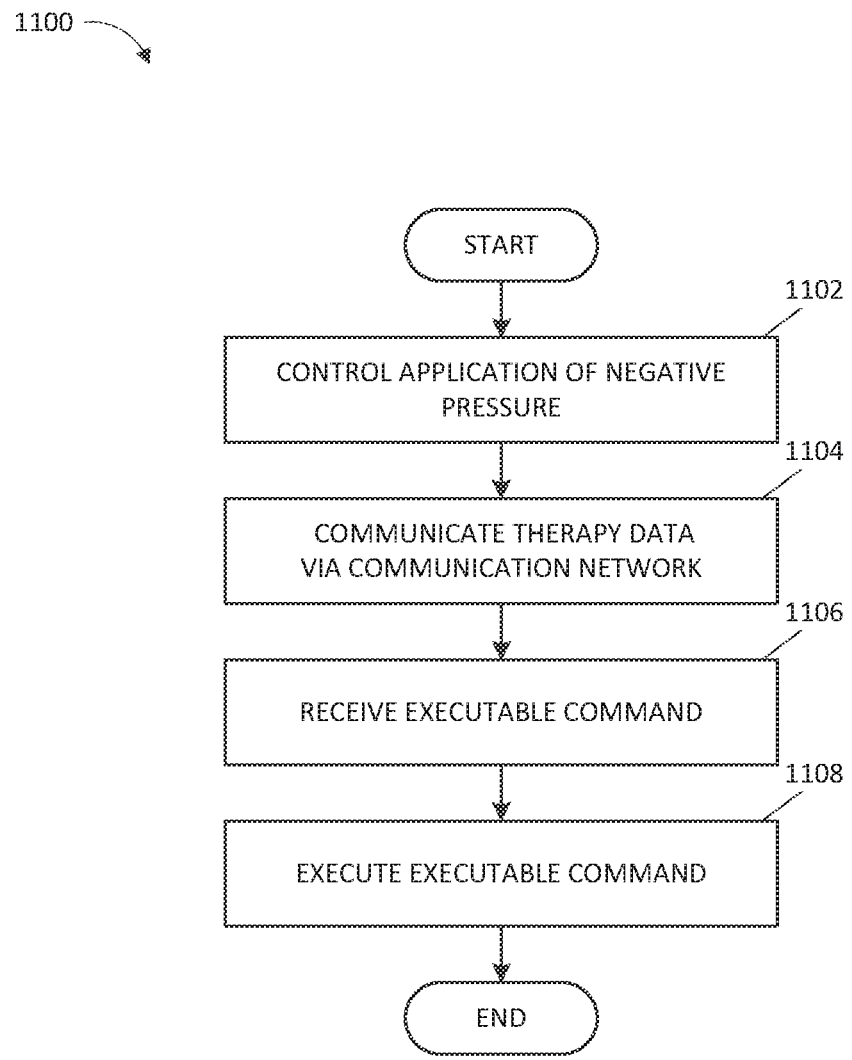
FIG. 11 illustrates a process performable by a pump assembly according to some embodiments.

FIG. 11 illustrates a process 1100 performable by a pump assembly, such as the pump assembly 230. For convenience, the process 1100 is described in the context of components of the pump assembly 300, but may instead be implemented in other systems described herein or by other systems not shown.

At block 1102, the process 1100 can control application of negative pressure. For example, the processor 310 can instruct and cause the pump control processor 370 to start or stop provision of negative pressure with the pump 390.

At block 1104, the process 1100 can communicate therapy data via a communication network. For example, the processor 310 can instruct and cause the communications processor 330 to wirelessly transmit therapy data indicative of a characteristic of wound therapy performed by the pump assembly 300 via the network 396 to the data processing system 394.

At block 1106, the process 1100 can receive an executable command. For example, the communications processor 330 can receive an executable command from the external device 392.

At block 1108, the process 1100 can execute the executable command. For example, the communications processor 330 can execute the executable command causing the communications processor 330 to perform one or more operations, such as to test an operation of the communications processor 330, transmit hardware or software version data for the communications processor 330, change a setting associated with operation of the communications processor 330, or transition from communicating therapy data one communication network to a different communication network. The communications processor 330 moreover may execute the command without the processor 310 processing the executable command or without providing the executable command to the processor 310.

Other Variations and Terminology

The communications processor 330 of FIG. 3A can permit interrogation or reprogramming of the communications processor 330 via manual user interactions with the pump assembly 300, such as via user inputs to interface elements (such as, buttons or zones of a touchscreen) of the processor 310 or the input/output (I/O) module 320. In one example, a display of the pump assembly, such as the display 206, can present a terminal program (for instance, PuTTY HyperTerminal). User inputs to the display or one or more other interface elements can be received by the terminal program and used by the terminal program to generate and provide an executable command (such as, an AT command [which may for instance be in accordance with one or more standards like 3GPP TS 34.121 (WCDMA), 3GPP TS 51.010 (GSM without EGRPS) and 3GPP TS51.010 (GSM with EGRPS)] or a command of a Hayes command set) to the communications processor 330 for execution. The terminal program can display any responses from the communications processor 330, such as the results of execution of the executable command. The communications processor 330 can receive and execute the executable command from the terminal program without interrupting wound therapy being performed by the pump assembly 300 or without at least some components or features of the pump assembly 300 (for instance, powered or activated). The executable command may, in some embodiments, instruct and cause the communications processor 330 to: test an operation of the communications processor 330, transmit the hardware or software version data for the communications processor 330 to the display for presentation, change a setting associated with operation of the communications processor 330, communicate data via one communication network rather than another communication network, perform an operation associated with a communication network over which the communications processor 330 transmits data, or the like.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed:

1. An apparatus for applying negative pressure to a wound, the apparatus comprising:
   a housing;
   a negative pressure source at least partially enclosed by the housing and configured to provide negative pressure via a fluid flow path to a wound dressing;
   a first circuit board assembly at least partially enclosed by the housing and comprising a first controller configured to control a wound therapy with the wound dressing by activation and deactivation of the negative pressure source; and
   a second circuit board assembly at least partially enclosed by the housing and in communication with the first circuit board assembly, the second circuit board assembly being separate from the first circuit board assembly and comprising a second controller configured to:
      communicate therapy data via a communication network, the therapy data being indicative of a characteristic of the wound therapy,
      receive an executable command from an electronic device via a bus electrically connecting the second controller and the electronic device, and
      execute the executable command without providing the executable command to the first controller.

2. The apparatus of claim 1, wherein the second controller is configured to receive the executable command from the electronic device via wireless communication.

3. The apparatus of claim 1, wherein the second controller is configured to wirelessly communicate the therapy data via the communication network.

4. The apparatus of claim 1, wherein the electronic device is not supported by the housing.

5. The apparatus of claim 1, wherein the second controller is configured to receive and execute the executable command without the wound therapy being interrupted.

6. The apparatus of claim 1, wherein the second controller is configured to receive and execute the executable command to test an operation of the second controller.

7. The apparatus of claim 1, wherein the second controller is configured to receive and execute the executable command despite the first controller not being operational.

8. The apparatus of claim 1, wherein the executable command comprises a request for hardware or software version data, and execution of the executable command by the second controller causes the second controller to transmit the hardware or software version data to the electronic device.

9. The apparatus of claim 1, wherein execution of the executable command by the second controller causes the second controller to change a setting associated with operation of the second controller.

10. The apparatus of claim 1, wherein execution of the executable command by the second controller causes the second controller to communicate the therapy data via another communication network rather than the communication network.

11. The apparatus of claim 1, wherein execution of the executable command by the second controller causes the second controller to perform an operation associated with the communication network.

12. The apparatus of claim 1, wherein the executable command is an attention (AT) command or a command of a Hayes command set.

13. The apparatus of claim 1, wherein the second circuit board assembly comprises a modem that includes the second controller.

14. The apparatus of claim 1, wherein the second controller is configured to enter (i) a data mode in which data processed by the second controller is not executed and (ii) a command mode in which data processed by the second controller is executed.

15. The apparatus of claim 1, further comprising:
a connector port supported by the housing and configured to electrically connect the electronic device and the bus; and
a switch connected to the bus and configured to, in a first position, electrically connect the first controller to the second controller and, in a second position, electrically connect the connector port to the second controller.

16. The apparatus of claim 1, further comprising:
a connector port supported by the housing and configured to electrically connect the electronic device and the bus;
a first circuit component configured to electrically connect the first controller and the second controller in a first mode of operation; and
a second circuit component configured to electrically connect the connector port and the second controller in a second mode of operation,
wherein, in the second mode of operation, the first circuit component is configured to not electrically connect the first controller and the second controller, and
wherein, in the first mode of operation, the second circuit component is configured to not electrically connect the connector port and the second controller.

17. A method of operating a wound therapy device comprising a first circuit board assembly and a second circuit board assembly separate from the first circuit board assembly, the method comprising:
by a first controller mounted to the first circuit board assembly:
controlling application of negative pressure with a pressure source to a wound dressing; and
by a second controller mounted to the second circuit board assembly:
communicating therapy data via a communication network, the therapy data being indicative of a characteristic of a wound therapy performed with the pressure source,
receiving an executable command from an electronic device via a bus electrically connecting the second controller and the electronic device, and
executing the executable command without processing the executable command with the first controller.

18. The method of claim 17, further comprising receiving another executable command from the electronic device via wireless communication.

19. The method of claim 17, wherein said receiving and executing comprises receiving and executing the executable command without the wound therapy being interrupted.

20. The method of claim 17, wherein said executing comprises executing the executable command to test an operation of the second controller or change a setting associated with operation of the second controller.

21. The method of claim 17, wherein said receiving and executing comprises receiving and executing the executable command despite the first controller not being operational.

22. The method of claim 17, further comprising transitioning from operating in a first mode in which the second controller is electrically connected to the first controller and not electrically connected to the electronic device to operating in a second mode in which the second controller is electrically connected to the electronic device and not electrically connected to the first controller.

* * * * *

UNITED STATES PATENT AND TRADEMARK OFFICE
CERTIFICATE OF CORRECTION

PATENT NO. : 11,712,508 B2  
APPLICATION NO. : 16/629190  
DATED : August 1, 2023  
INVENTOR(S) : William W. Gregory et al.

Page 1 of 1

It is certified that error appears in the above-identified patent and that said Letters Patent is hereby corrected as shown below:

In the Specification

In Column 4, Line 66, delete "Moreover;" and insert --Moreover,--.

In Column 5, Line 15, delete "herein;" and insert --herein,--.

In Column 5, Line 39, delete "Renays" and insert --Renasys--.

In Column 5, Lines 63-64, delete "superabsorbing" and insert --super absorbing--.

In Column 8, Line 26, delete "800" and insert --800 mL--.

In Column 9, Line 31, delete "904," and insert --904.--.

In Column 9, Line 61, delete "320," and insert --320.--.

In Column 13, Line 38, delete "830," and insert --830.--.

In Column 13, Line 60, delete "810," and insert --810.--.

Signed and Sealed this  
Twenty-sixth Day of September, 2023

Katherine Kelly Vidal  
*Director of the United States Patent and Trademark Office*